US008974369B2

(12) United States Patent
Tomlinson, Jr.

(10) Patent No.: US 8,974,369 B2
(45) Date of Patent: Mar. 10, 2015

(54) PELVIC HARNESS AND METHOD OF MANUFACTURING SAME

(71) Applicant: Daniel H Tomlinson, Jr., Duarte, CA (US)

(72) Inventor: Daniel H Tomlinson, Jr., Duarte, CA (US)

(*) Notice: Subject to any disclaimer, the term of this patent is extended or adjusted under 35 U.S.C. 154(b) by 271 days.

(21) Appl. No.: 13/673,893

(22) Filed: Nov. 9, 2012

(65) Prior Publication Data

US 2013/0131442 A1   May 23, 2013

Related U.S. Application Data

(60) Provisional application No. 61/563,440, filed on Nov. 23, 2011.

(51) Int. Cl.
*A61F 5/00*      (2006.01)
*A61F 2/78*      (2006.01)
*A61H 19/00*     (2006.01)

(52) U.S. Cl.
CPC *A61F 2/78* (2013.01); *A61H 19/50* (2013.01); *A61H 19/44* (2013.01); *A61H 2201/165* (2013.01); *A61H 2201/1685* (2013.01); *A61H 19/32* (2013.01)
USPC .......................................................... 600/38

(58) Field of Classification Search
CPC .......... A61F 2/78; A61H 19/30; A61H 19/32; A61H 19/44; A61H 19/50
USPC ........................................................ 600/38–41
See application file for complete search history.

(56) References Cited

U.S. PATENT DOCUMENTS

| | | | |
|---|---|---|---|
| 4,440,183 A * | 4/1984 | Miller | 600/41 |
| 5,690,603 A | 11/1997 | Kain | |
| 5,853,362 A | 12/1998 | Jacobs | |
| 6,749,558 B1 * | 6/2004 | Brintle | 600/38 |
| 6,793,620 B1 | 9/2004 | Droznin | |
| 6,849,041 B2 * | 2/2005 | Astin | 600/38 |

* cited by examiner

*Primary Examiner* — John Lacyk
(74) *Attorney, Agent, or Firm* — Loza & Loza, LLP; Razmig Messerian

(57) ABSTRACT

One feature pertains to a pelvic harness comprising a tab having a first surface that is adapted to secure to at least a portion of a superior pubic skin region, and a saddle having a first surface adapted to secure to at least a portion of a perineal-anal region. The tab may be positioned at a first end of the pelvic harness, and the saddle may be positioned at a second, opposite end of the pelvic harness. The pelvic harness may further comprise a frame having a first end and a second end, where the frame's first end is coupled to the tab and the second end is coupled to the saddle. A portion of the frame may form an opening positioned in between the tab and the saddle. The frame may include a rail portion that includes at least two rails that define the opening.

20 Claims, 25 Drawing Sheets

PELVIC HARNESS AND METHOD OF MANUFACTURING SAME

CLAIM OF PRIORITY

The present application for patent claims priority to U.S. Provisional Patent Application No. 61/563,440 entitled "PELVIC HARNESS" filed Nov. 23, 2011, the entire disclosure of which is hereby expressly incorporated by reference herein

BACKGROUND

1. Field

Various embodiments of the present disclosure pertain generally to pelvic harnesses and methods of manufacturing the same.

2. Background

Generally, a dildo is a device that may be used during sexual activity for anal, vaginal, and/or oral stimulation. Dildos may be made of a variety of materials, including silicone, rubber, plastic, wood, glass, metal, etc., and are generally elongate in shape. Commonly, dildos may incorporate design features imitative of a human penis (e.g., glans, veins, etc.), but they may also be shaped to mimic a wide range of other objects including artificial and natural designs. In some cases, the distal end of a dildo may have a handle or other means for attachment to a stationary or moving object, or to the surface of a partner's body. In use dildos are inserted into the mouth, vagina, and/or anus, either by an individual or by a partner, using suitable lubrication as required. They provide stimulation from friction upon manipulation of the object, or by pressure from the distension of the cavity due to the volume of the object.

Dildos may be used by two or more people to give sexual pleasure to one another, either in lieu of or in addition to vaginal/penile or other modes of sexual congress. Dildos may also be used individually by either men or women. In addition to their use for pleasure, dildos may also be used for other purposes such as contraception, disease avoidance, disability, erectile dysfunction, temporary fatigue, and medical treatment.

A person holding and manipulating a dildo by hand may be inconvenienced and constrained from sexual activity. However, in some cases the dildo may be a "strap-on" dildo that attaches to the user's body via a strap and/or harness that allows for hands-free manipulation of the dildo. As one example, the strap-on dildo may be attached to the user's pelvic region and be manipulated by the user through pelvic thrusts. Strap-on dildos are made in a wide variety of styles, with variations in how the harness fits the user, how the dildo attaches to the harness, as well as various features intended to facilitate stimulation of the user or a sexual partner of the user.

In some cases, a strap-on dildo may feature a penis prosthetic aid (e.g., penis prosthetic attachment) that is, at least partially, hollow on the inside, and has an opening at the distal end adapted to receive a user's penis. Such penis prosthetic attachments may also be known as extenders, extensions, and/or penis sleeves. The user, who may, for example, suffer from a medical condition such as erectile dysfunction, may wear the extender over his penis by inserting his penis into the extender's opening to achieve an increased effective penis length and/or girth depending on the dimensions of the extender.

Various types of harnesses may be used with strap-on dildos. For example, a two-strap harness, may be similar to a g-string in that one strap goes around the user's waist, like a belt, while the other goes between the user's legs and connects to the other strap in the middle near the lower back. While two-strap harnesses are simple in their design, some users may find them uncomfortable to wear because the strap may rub against the anus (along with possibly other sensitive areas), and afford limited stability to the attached dildo. As another example, a three-strap harness may include one strap around the user's waist, and two more straps that each wrap around the user's thighs. The straps that wrap around the thighs couple to the first strap near, for example, the front portion of the first strap near the pubic region of the user where the dildo may be positioned. Other types of strap-on dildos having additional straps (e.g., four-strap, five-strap, etc.) are commonly found in the prior art as well. However, some users may find the one or more straps of a strap-on dildo uncomfortable, unsightly, unpleasing to the touch, and/or cumbersome to implement.

U.S. Pat. No. 5,690,603 (issued to "Kain") discloses an erogenic stimulator that may be considered a type of "strapless" strap-on dildo. The erogenic stimulator features a bulb at one end adapted to fit inside of a vagina or anus and serves to secure the erogenic stimulator to the user's pubic region. Once the bulb is inserted into the user's vagina/anus, it is substantially held in place by the user's muscles. However, some users may find inserting the bulb into their anus or vagina uncomfortable. Moreover, coupling the erogenic stimulator to a male user's anus may prove difficult or fruitless because the user's testicles and penis may impede use of the phallic end of the erogenic stimulator for sexual activity with a partner.

U.S. Pat. No. 6,793,620 (issued to "Droznin et al.") discloses a strapless male sexual aid that features a hollow penis prosthetic aid coupled to a strap that wraps around the testicles of the user to secure the sexual aid to the user's genitalia. However, the aforementioned sexual aid may suffer from stability issues. Specifically, the sexual aid may have a limited ability to keep the penis prosthetic aid at an upward, erect angle preferred for sexual intercourse, and instead the sexual aid may unintentionally droop downward, particularly if the biological penis inserted into the hollow penis prosthetic aid is flaccid. Moreover, some users may find the strap that wraps around the testicles to be uncomfortable.

Thus, there is a need for a pelvic harness that securely couples one or more objects, such as a dildo, extender, and/or plug, to the pelvic region of a user and does not necessitate the use of straps. The objects coupled may be designed for the pleasure of the user's partner or both the user's partner and the user. The desired pelvic harness should also provide improved stability and comfort over prior art strapless sexual devices. Moreover, there is a need for a pelvic harness that may accommodate the testicles and/or penis of a user while securing an object, such as a dildo, extender, and/or plug, to the pelvic region of the user.

SUMMARY

One feature provides a pelvic harness that comprises a tab having a first surface that is adapted to secure to at least a portion of a superior pubic skin region, the tab positioned at a first end of the pelvic harness, and a saddle having a first surface adapted to secure to at least a portion of a perineal-anal region, the saddle positioned at a second, opposite end of the pelvic harness. According to one embodiment, the pelvic harness further comprises an opening positioned in between the tab and the saddle, where the opening is adapted to allow at least one of a penis or a scrotum to pass through the opening to secure the pelvic harness to a pelvic region. According to another embodiment, a second surface of the tab is adapted to couple to a dildo, where the second surface of the tab is opposite to the first surface of the tab. According to yet another embodiment, the pelvic harness further comprises a frame having a first end and a second end, and the frame's first end is coupled to the tab and the frame's second end is coupled to the saddle, wherein a portion of the frame forms an opening positioned in between the tab and the saddle.

According to one embodiment, the opening is adapted to allow at least one of a penis or a scrotum to pass through the opening to secure the pelvic harness to a pelvic region. According to another embodiment, the frame is flexible and adapted to bend in response to a force exceeding a predefined threshold to allow the pelvic harness to fit one or more contours of a pelvic region. According to yet another embodiment, the frame comprises a wire loop having a first end encased within the tab and a second end encased within the saddle, and a rail portion of the wire loop not encased by the tab or the saddle forms at least two rails that define, in part, the opening.

According to one embodiment, the frame comprises at least two wires each having a first end encased within the tab and a second end encased within the saddle, and a rail portion of the two wires not encased by the tab or the saddle defines, in part, the opening. According to another embodiment, the frame comprises a rail portion that includes at least two rails that define, in part, the opening, and at least a first rail of the two rails is adapted to removeably couple to at least one rail accessory to secure the rail accessory to the pelvic harness. According to yet another embodiment, the rail accessory includes an accessory base having at least one rail receiver that removeably couples to the first rail, and the rail accessory further includes a secondary accessory coupled to the accessory base.

According to one embodiment, the secondary accessory is a secondary dildo adapted to be inserted into an anus or a vagina of a user wearing the pelvic harness. According to another embodiment, the secondary accessory is an extender erection accessory having an elongate shaft, the elongate shaft having a distal end that couples to the accessory base and a proximal end that is adapted to be inserted into a cavity of an extender dildo, the extender dildo coupled to a second surface of the tab, the extender erection accessory adapted to provide rigidity to the extender dildo. According to yet another embodiment, the elongate shaft has a curved cross section that forms an extender accessory cavity that is adapted to receive a penis, the extender accessory cavity allowing the penis and the extender erection accessory to both be inserted into the cavity of the extender dildo.

Another feature provides a pelvic harness that comprises a tab having a first surface that couples to an area of skin associated with at least one of a hypogastrium, a pubic symphysis, or a pubis bone, a saddle having a first surface adapted to secure to at least a portion of a perineal-anal region, and an opening in between the tab and the saddle, the opening adapted to allow at least one of a penis or a scrotum to pass through the opening to secure the pelvic harness to a pelvic region without straps. According to one embodiment, the first surface of the saddle is convex having a vertex that secures to the portion of the perineal-anal region. According to another embodiment, the pelvic harness further comprises a frame having a first end and a second end, the frame's first end coupled to the tab and the frame's second end coupled to the saddle, wherein a portion of the frame forms the opening in between the tab and the saddle. According to yet another embodiment, the frame is flexible to allow the tab to bend or twist relative to the saddle. According to yet another embodiment, the frame comprises a rail portion that includes at least two rails that define, in part, the opening, and at least a first rail of the two rails is adapted to removeably couple to at least one rail accessory to secure the rail accessory to the pelvic harness.

Another feature provides a method of manufacturing a pelvic harness where the method comprises providing a tab having a first surface that is adapted to couple to at least a portion of a superior pubic skin region, providing a saddle having a first surface that is adapted to couple to least a portion of a perineal-anal region, providing a frame having an opening adapted to allow at least one of a penis or a scrotum to pass through the opening to secure the pelvic harness to a pelvic region without straps, coupling a first end of the frame to the tab, and coupling a second end of the frame to the saddle. According to one embodiment, the frame comprises a first rail, and the method further comprises providing a rail accessory that includes a rail accessory base and a secondary accessory, the rail accessory base having a rail receiver, and removeably coupling the rail receiver to the first rail to secure the rail accessory to the pelvic harness, the secondary accessory being one of a secondary dildo or an extender erection accessory.

DETAILED DESCRIPTION

In the following description numerous specific details are set forth in order to provide a thorough understanding of the invention. However, one skilled in the art would recognize that the invention might be practiced without these specific details. In other instances, well known methods, procedures, and/or components have not been described in detail so as not to unnecessarily obscure aspects of the invention.

In the following description, certain terminology is used to describe certain features of one or more aspects of the disclosure. For example, the term "exemplary" as used herein is defined as serving as one example or illustration. The term "dildo" is any elongate device that may be used during sexual activity for anal, vaginal, and/or oral stimulation, and may also include penis prosthetic attachments such as extenders and "penis sleeves." All anatomical parts and/or regions described herein refer to human anatomical parts and/or regions. These anatomical parts and/or regions include, but are not limited to, skin, bone, penises, scrotums, vaginas, testes, perinea, perineal-anal regions, anuses, coccyges, vaginal fourchette, pelvic regions, pubic regions, superior pubic skin regions, etc.

As used herein, the term "superior pubic skin region" includes any portion of the skin between the navel and the penis in a male and the vulva in a female. As used herein, the term "perineum" refers to: (1) the area of skin between the anus and the scrotum of a male, and (2) the area of skin between the anus and the fourchette of the vulva in a female. As used herein, the term "perineal-anal region" includes the perineum (as defined above), the anus, the intergluteal cleft, and the buttocks.

Overview

Figure 1:
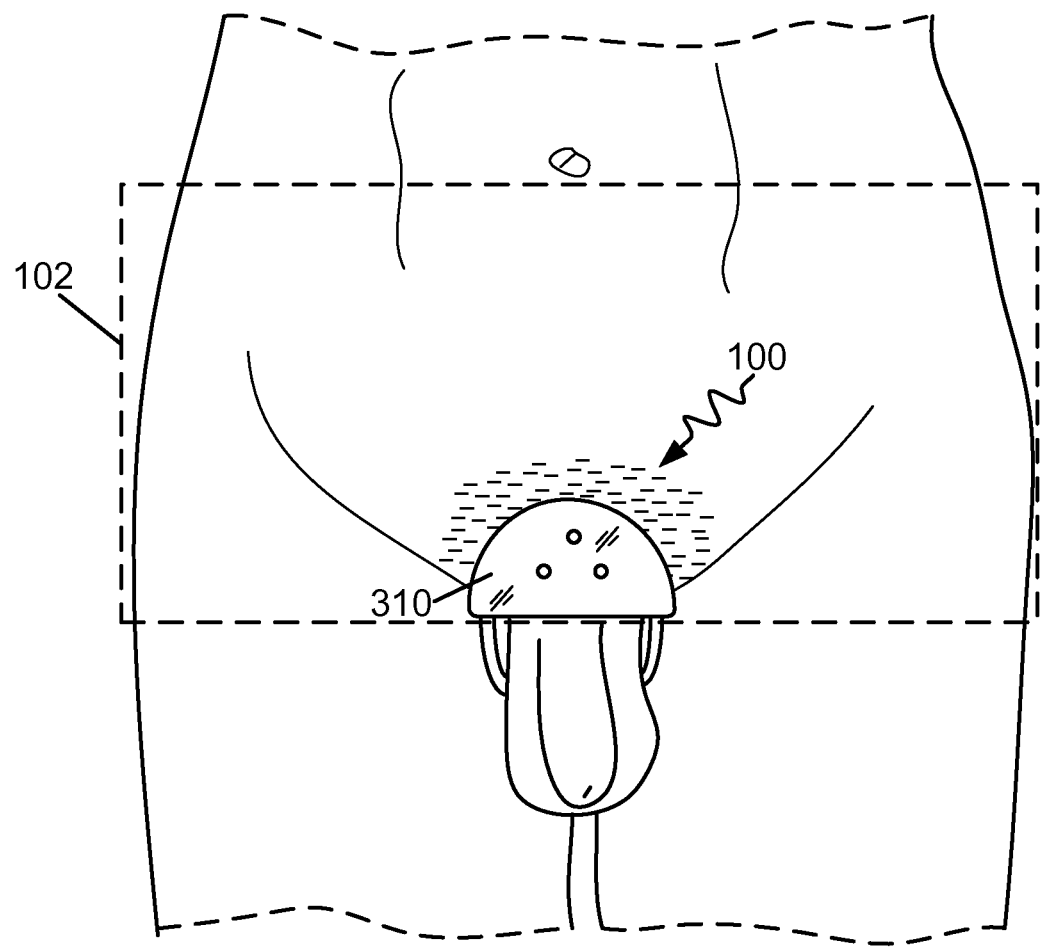
FIG. 1 illustrates a front view of a male user wearing a pelvic harness that couples to the pelvic region of a user.

FIG. 1 illustrates a front view of a male user wearing a novel pelvic harness 100 that couples to the pelvic region of a user according to one embodiment. As explained in greater detail below, the pelvic harness 100 may couple to, among other things, one or more dildos that can be used to enhance sexual activity. In the illustrated example, the strapless pelvic harness 100 is secured to the user's body without a waist strap. For example, the pelvic harness 100 includes a tab 310 that is secured against a portion of the user's superior pubic skin region 102.

Figure 2:
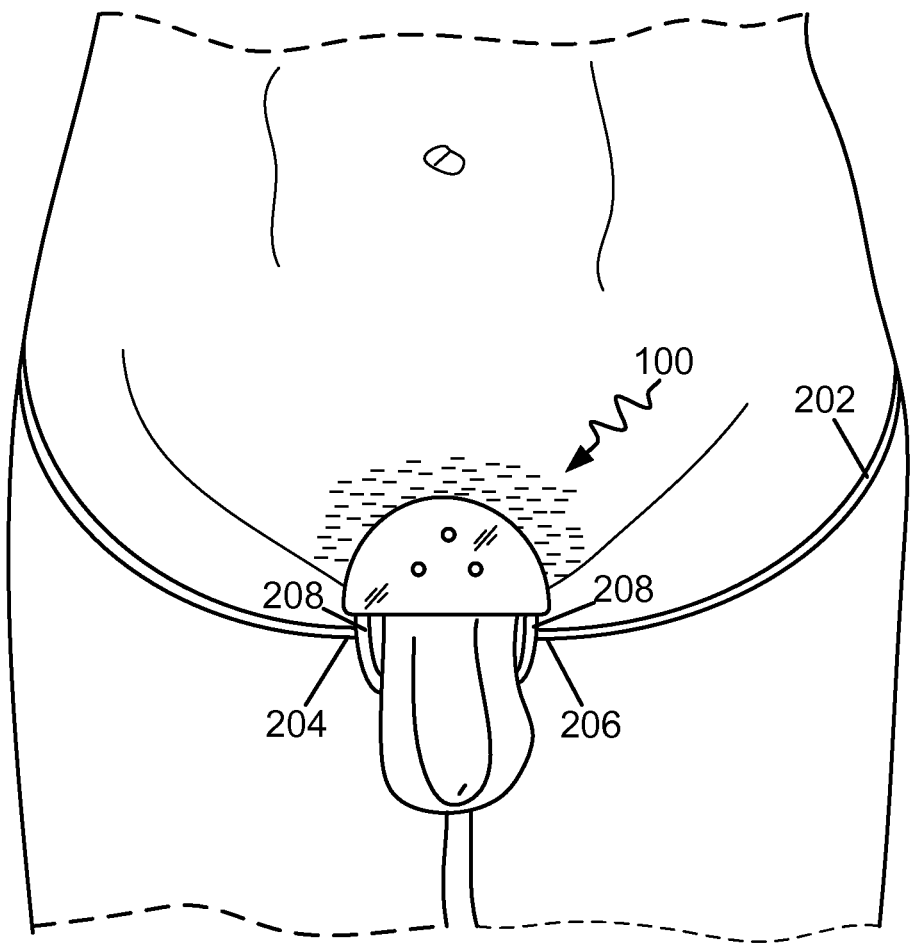
FIG. 2 illustrates a pelvic harness that is secured to a male user using a thin waist strap having ends that are removeably coupled to the sides of the pelvic harness.

FIG. 2 illustrates another embodiment where the pelvic harness 100 is further secured to the male user using a thin waist strap 202 having ends 204, 206 that are removeably coupled to the sides 208 of the pelvic harness 100.

Pelvic Harness

Figure 3:
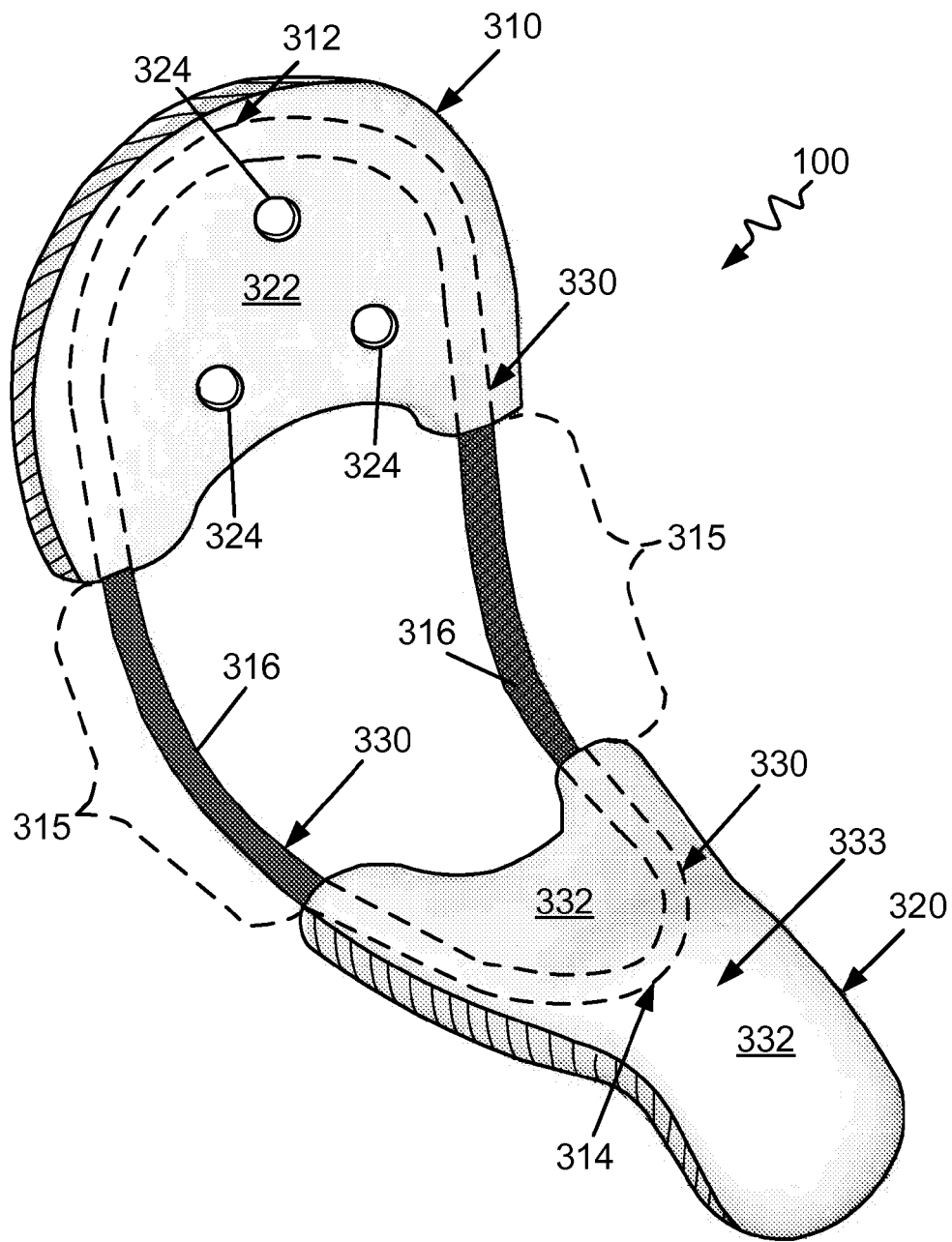
FIGS. 3 and 4 illustrate front and rear perspective views, respectively, of a pelvic harness.
Figure 4:
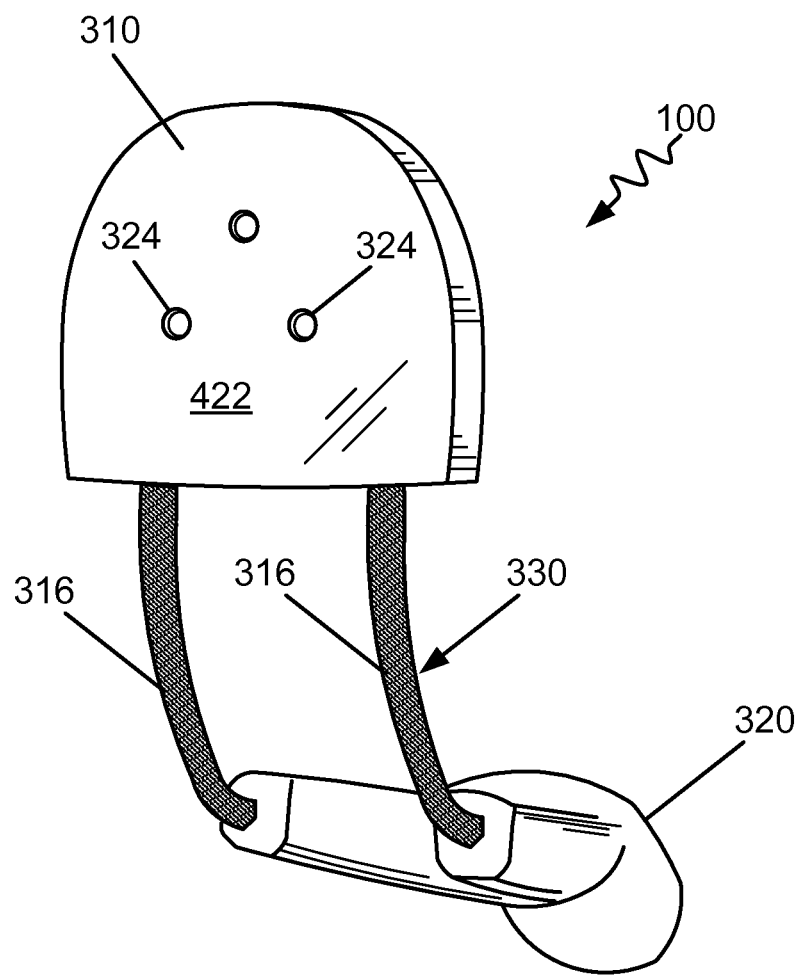

FIGS. 3 and 4 illustrate front and rear perspective views, respectively, of the pelvic harness 100 according to one embodiment. Referring to FIG. 3, the pelvic harness 100 may comprise a tab 310, a saddle 320, and a frame 330. The tab 310 may be comprised of a rigid or semi-rigid material, such as, but not limited to, plastic, silicone, wood, and/or metal, and may be molded around a first end 312 of the frame 330. The tab 310 features a first surface 322 that is adapted to press against and secure to a user's superior pubic skin region. For example, the first surface 322 may press against and secure to (e.g., couple to) a region of the user's body just above the user's genitalia, including, but not limited to, the skin over the pubic symphysis, pubis, and/or superior pubic rami of the user. According to one example, the first surface 322 may couple to an area of skin associated with (e.g., covering) the hypogastrium, the pubic symphysis, and/or pubis bone.

Referring to FIG. 4, the tab 310 also features a second surface 422 that is on the opposite side of the tab's first surface 322. The second surface 422 is adapted to secure to a dildo (not shown in FIGS. 3 and 4), such as, but not limited to, an extender. The tab 310 may include one or more holes 324 that assist with securing the second surface 422 to the dildo. For example, an adhesive material commonly used for plastics and silicon may be applied to the second surface 422 and/or the cavities formed by the holes 324. Then, the second surface 422 may adhere to a corresponding surface of the dildo. According to one embodiment, the holes 324 may be absent.

Referring to FIG. 3, the saddle 320 may also be comprised of a rigid or semi-rigid material, such as, but not limited to, plastic, silicone, wood, and/or metal, and may be molded around a second end 314 of the frame 330. The saddle 320 features a first surface 332. At least a portion of the first surface 332 is adapted to press against at least a portion of the user's perineal-anal region. For example, for a male user the saddle's first surface 332 may press against (e.g., secure to) the intergluteal cleft, the buttocks, the skin covering the coccyx, the area of skin between the coccyx and the anus, the anus, and/or the area of skin in between the anus and the scrotum. For a female user the saddle's first surface 332 may press against (e.g., secure to) the intergluteal cleft, the buttocks, the skin covering the coccyx, the area of skin between the coccyx and the anus, the anus, and/or the area of skin in between the anus and the fourchette of the vulva. In one embodiment, the first surface 332 is convex having a vertex 333 that secures to the perineal-anal region. According to one embodiment, the tab 310 and/or the saddle 320 may be covered or coated with a soft and/or smooth material, such as, but not limited to, plastic, glass, cotton, polyester, satin, silk, artificial or natural fur, plastic, and/or silicone for added comfort.

The frame 330 may serve to secure the tab 310 and the saddle 320 to each other and may be comprised of a metal or metal alloy. The first end 312 of the frame 330 may be coupled to the tab 310 and the second, opposing end 314 of the frame 330 may be coupled to the saddle 320, such that a portion of the frame 330 forms an opening positioned in between the tab 310 and the saddle 320. According to one embodiment, the frame 330 may be a wire loop where portions of the loop are embedded within the tab 310 and the saddle 320 (as illustrated by the dashed lines in FIG. 3). The metal or metal alloy used to construct the frame 330 should be of a sufficient gauge to allow the frame 330 to be rigid, yet also be bendable in response to a force exceeding a predefined threshold, such as, but not limited to 15 lbs. Bending the frame 330 allows a user to adjust the shape of the pelvic harness 100 to better fit one or more contours of the user's pelvic region.

The frame 330 may comprise a rail portion 315 that includes two or more rails 316 that are spaced apart to form an opening. The rails 316 may be spaced apart, and/or are able to be bent apart, wide enough to allow a male user to pass his scrotum and/or penis through the rails 316. A user may thus wear the pelvic harness 100 by first passing his scrotum and/or penis through the opening between the rails 316 so that the tab's first surface 322 comes into contact with the user's superior pubic skin region, and the saddle's first surface 332 comes into contact with at least a portion of the user's perineal-anal region. The rails 316 may be covered or coated with a soft and/or smooth material, such as, but not limited to, cotton, polyester, satin, silk, artificial or natural fur, plastic, and/or silicone for added comfort.

Figure 5A:
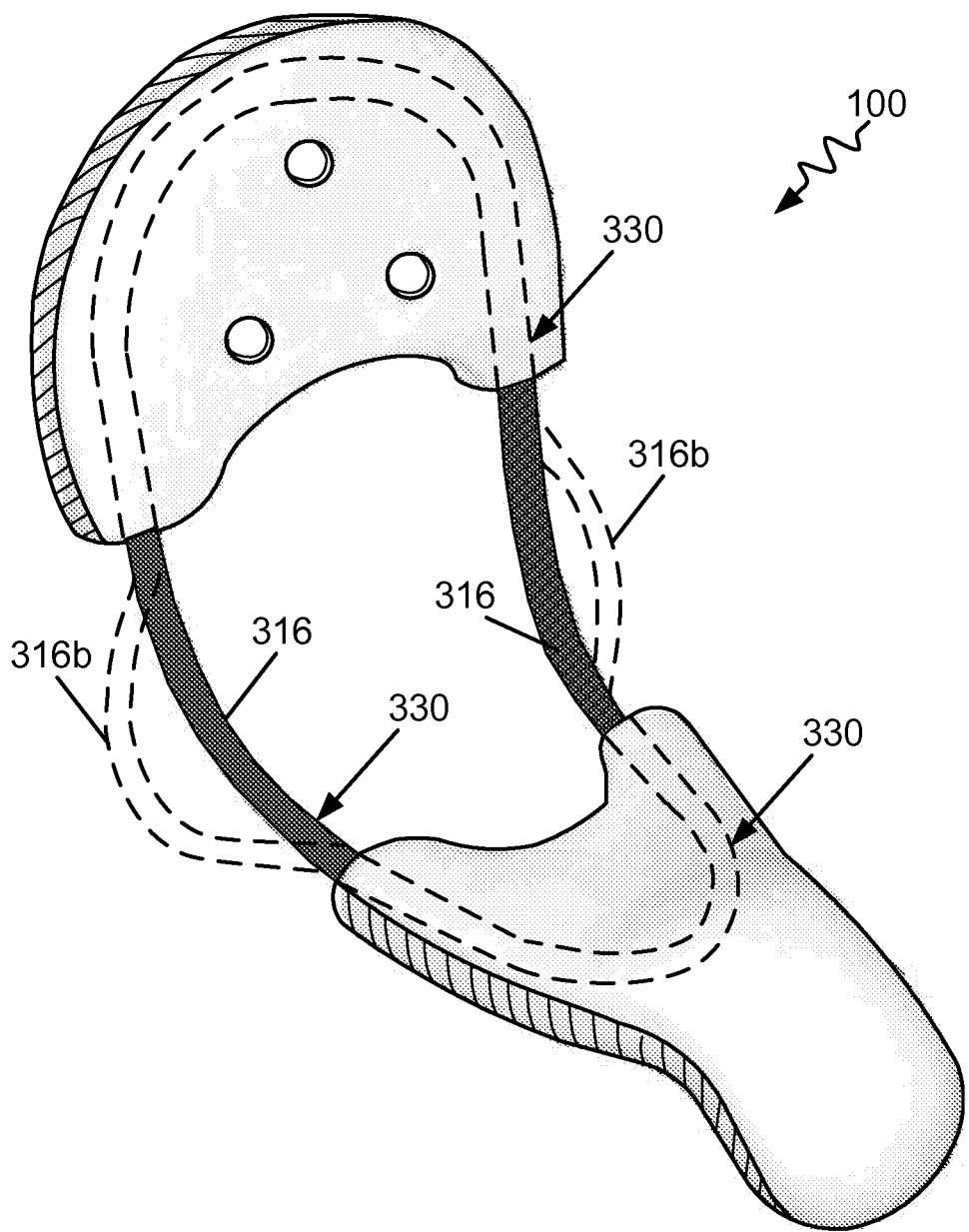
FIGS. 5A and 5B illustrate how rails of a pelvic harness frame may be bent apart and squeezed together in response to a force exceeding a specified threshold.
Figure 5B:
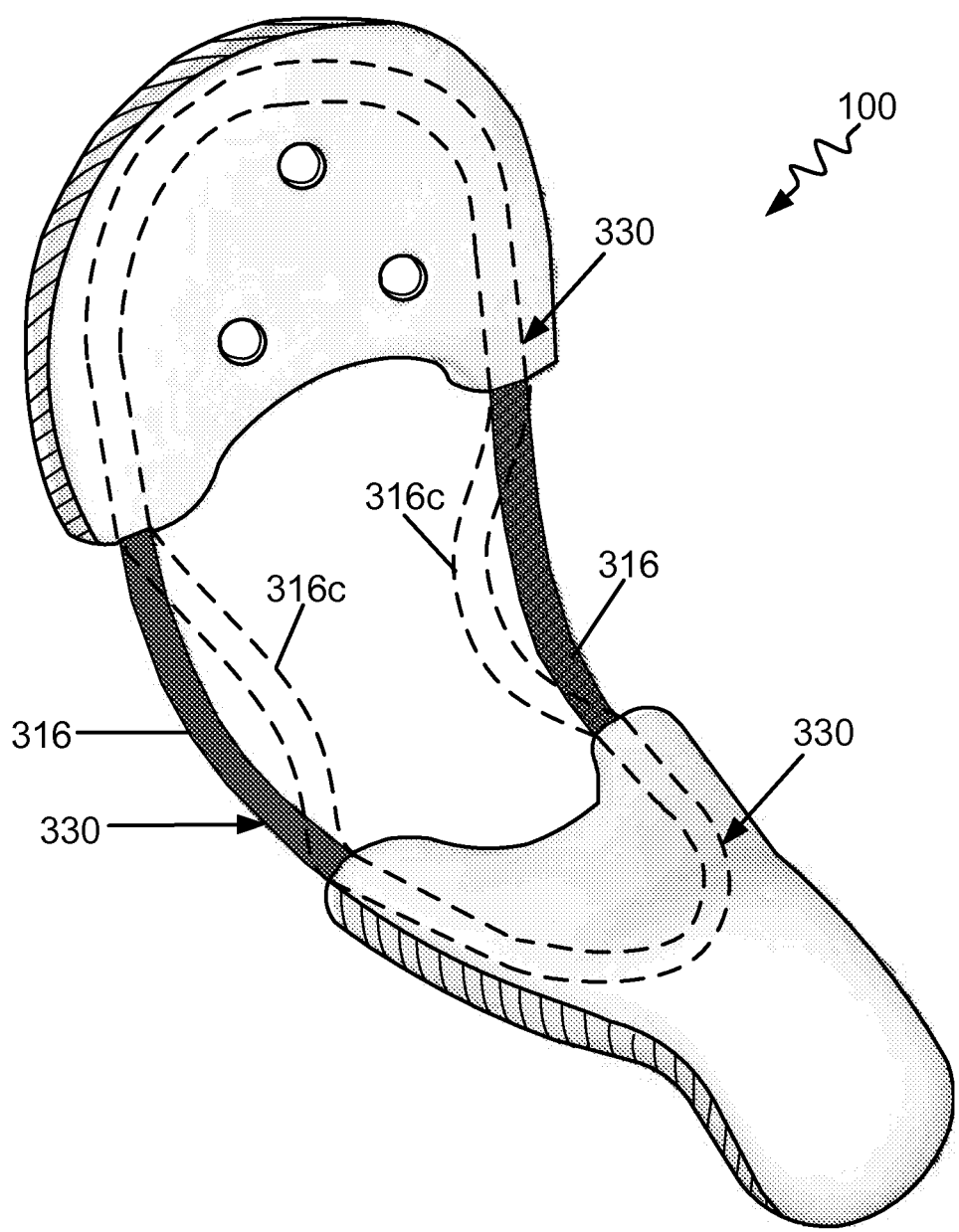

FIGS. 5A and 5B illustrate, according to one embodiment, how the rails 316 of the frame 330 may be bent apart and squeezed together in response to a force exceeding a specified threshold. Bending the rails 316 apart may allow a user to more easily and comfortably pass his scrotum and/or penis through the opening between the rails 316. Squeezing the rails 316 together may help secure the rails 316 snugly against the scrotum and/or penis of the user, thereby helping secure the pelvic harness 100. The material comprising the rails 316 may be rigid enough to maintain the shape of the pelvic harness 100 under normal use (e.g., during sexual activity), yet also be flexible enough to allow the rails 316 to elastically bend to create a wider or narrower opening. In FIG. 5A, the rails 316 are temporarily spaced further apart into a wider opening state (as indicated by the position of the rails 316b) thereby enlarging the opening to allow a user to more easily pass his scrotum and/or penis through. In FIG. 5C, the rails 316 are squeezed together into a narrower opening state (as indicated by the position of the rails 316c) thereby narrowing the opening between the rails to help secure the pelvic harness to the user's scrotum and/or penis. In another embodiment, the rails 316 are substantially stiff or inflexible and do not readily bend.

Figure 6:
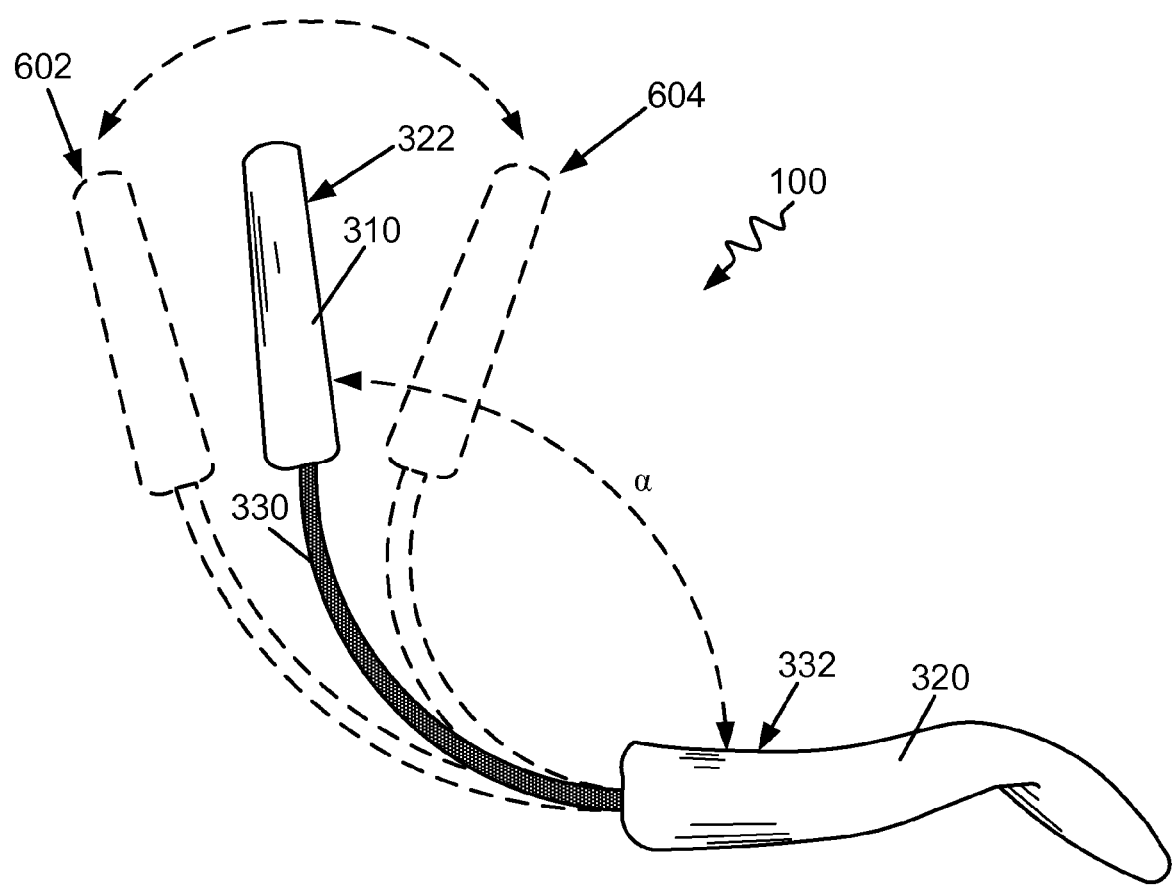
FIG. 6 illustrates a side view of a pelvic harness.

FIG. 6 illustrates a side view of the pelvic harness 100. As shown in the illustrated example, the frame 330 is comprised of a bendable/flexible metal or metal alloy that can be bent forward or backward so that the tab 310 may be bent toward, away from, and/or twist relative to the saddle 320. This allows the frame 330 to bend in response to a force exceeding a predefined threshold (e.g., greater than 15, 20, 25, 30, 35, 40, or 45 lbs) to allow the pelvic harness 100 to fit one or more contours of a user's pelvic region. For example, the tab 310 may be bent back, away from the saddle 320 so that the pelvic harness 100 is arranged in a first state 602. In another example, the tab 310 may be bent forward, toward the saddle 320 so that the pelvic harness 100 is arranged in a second state 604. According to one aspect, the frame 330 is flexible enough so that the first surface 322 of the tab 310 may be bent at an angle a relative to the first surface 332 of the saddle 320, where a ranges from 10 to 180 degrees.

Figure 7:
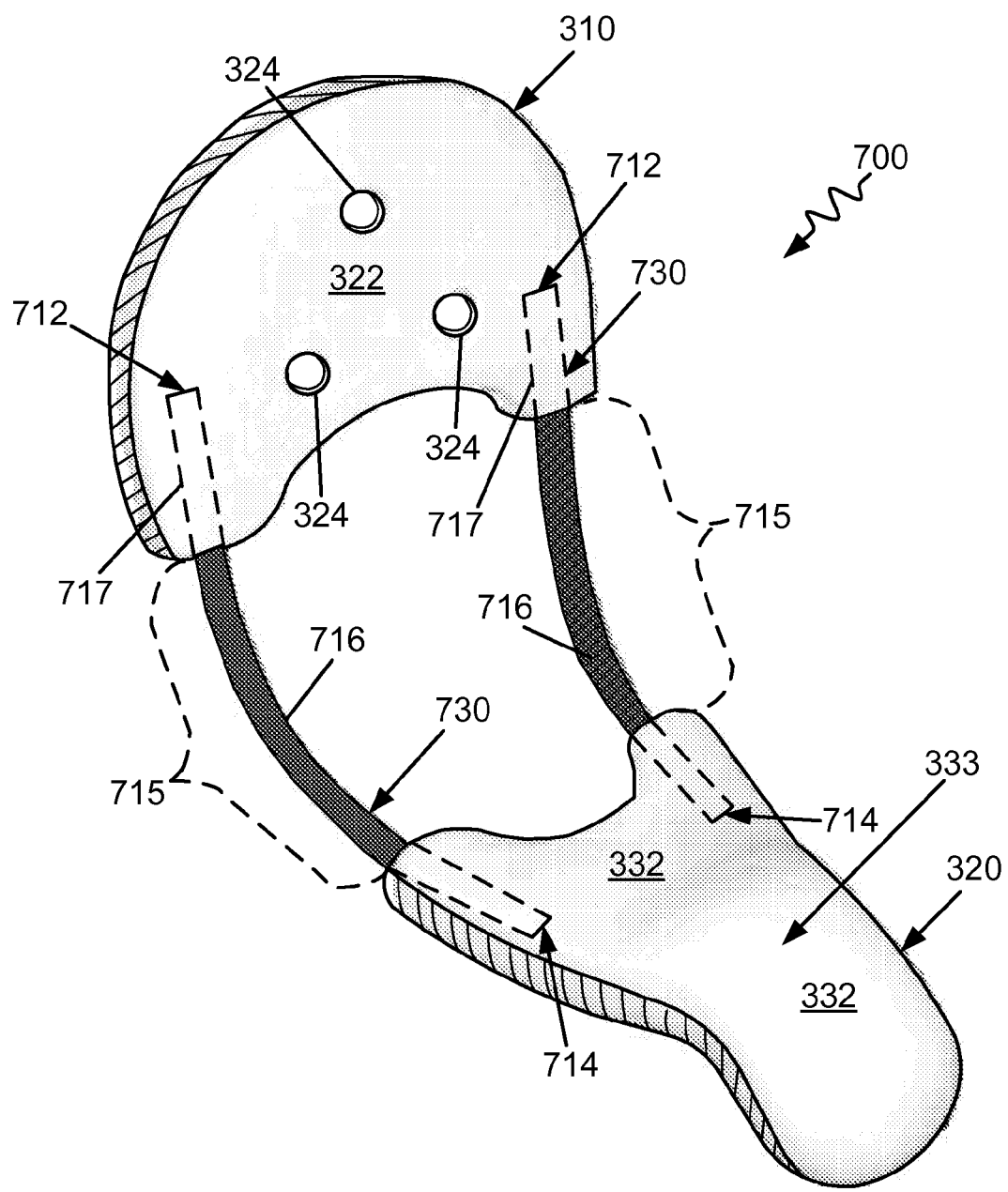
FIG. 7 illustrates another embodiment of a pelvic harness.

FIG. 7 illustrates another embodiment of a pelvic harness 700. In this example, the pelvic harness 700 is identical to the pelvic harness 100 shown in FIG. 3, except that its frame 730 is not a wire loop but instead it is comprised of at least two separate wires 717. Each wire 717 of the frame 730 includes a first end 712 coupled to the tab 310 and a second end 714 coupled to the saddle 320. The first end 712 and the second end 714 may be encased within the tab 310 and saddle 320, respectively. Like the frame 330 shown in FIG. 3, the frame 730 also includes a rail portion 715 comprising at least two rails 716 (i.e., each wire 717 includes a rail 716) that form an opening for a male user to slide his penis and/or testicles through. In one example, an adhesive, such as cyanoacrylate, may be used to further secure the ends 712, 714 of the wires 717 to the tab 310 and the saddle 320.

Pelvic Harness Coupled to a Dildo

Figure 8:
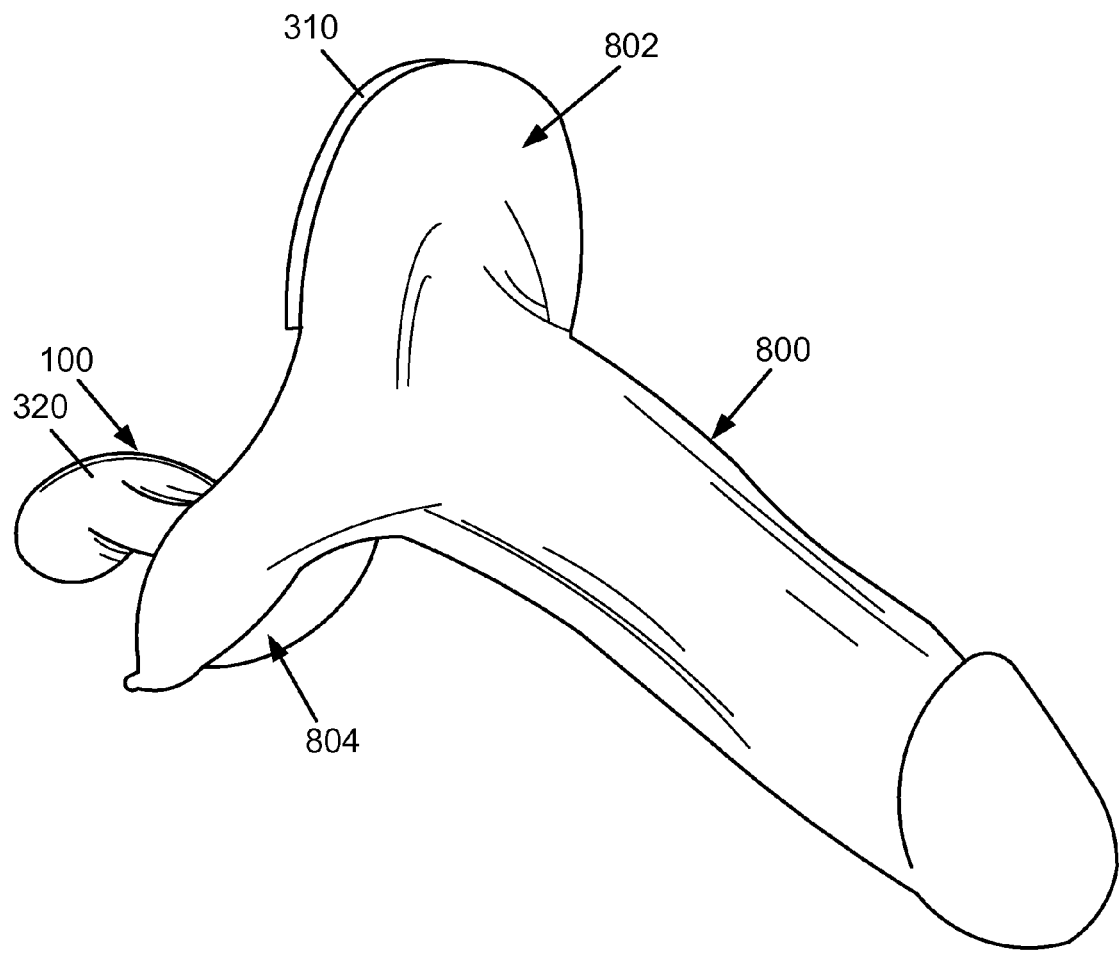
FIG. 8 illustrates a front perspective view of a pelvic harness coupled to a dildo.

FIG. 8 illustrates a front perspective view of the pelvic harness 100 coupled to a dildo 800 according to one embodiment. Specifically, the second surface 422 (see FIG. 4) of the pelvic harness' tab 310 is secured to a securement flap 802 of the dildo 800. In this example, the dildo 800 is an extender dildo (hereinafter referred to as an "extender") that is made of a soft silicone rubber and is meant to be worn over a user's biological penis and may also be used during sexual activity. However, in other embodiments, other types and shapes of dildos may be coupled to the second surface 422 of the tab 310, including solid dildos (i.e., not a hollow extender), simple cylindrical-shaped dildos (i.e., dildos not shaped like penises in that they lack a penis head), etc. In yet other embodiments, other devices, such as medical devices may be coupled and/or secured to the second surface 422 of the pelvic harness' tab 310. In the illustrated example, the dildo 800 includes a thin flap 804 near the base of the penis that is shaped like a portion of a scrotum. Of course, other embodiments may lack this flap 804.

Figure 9:
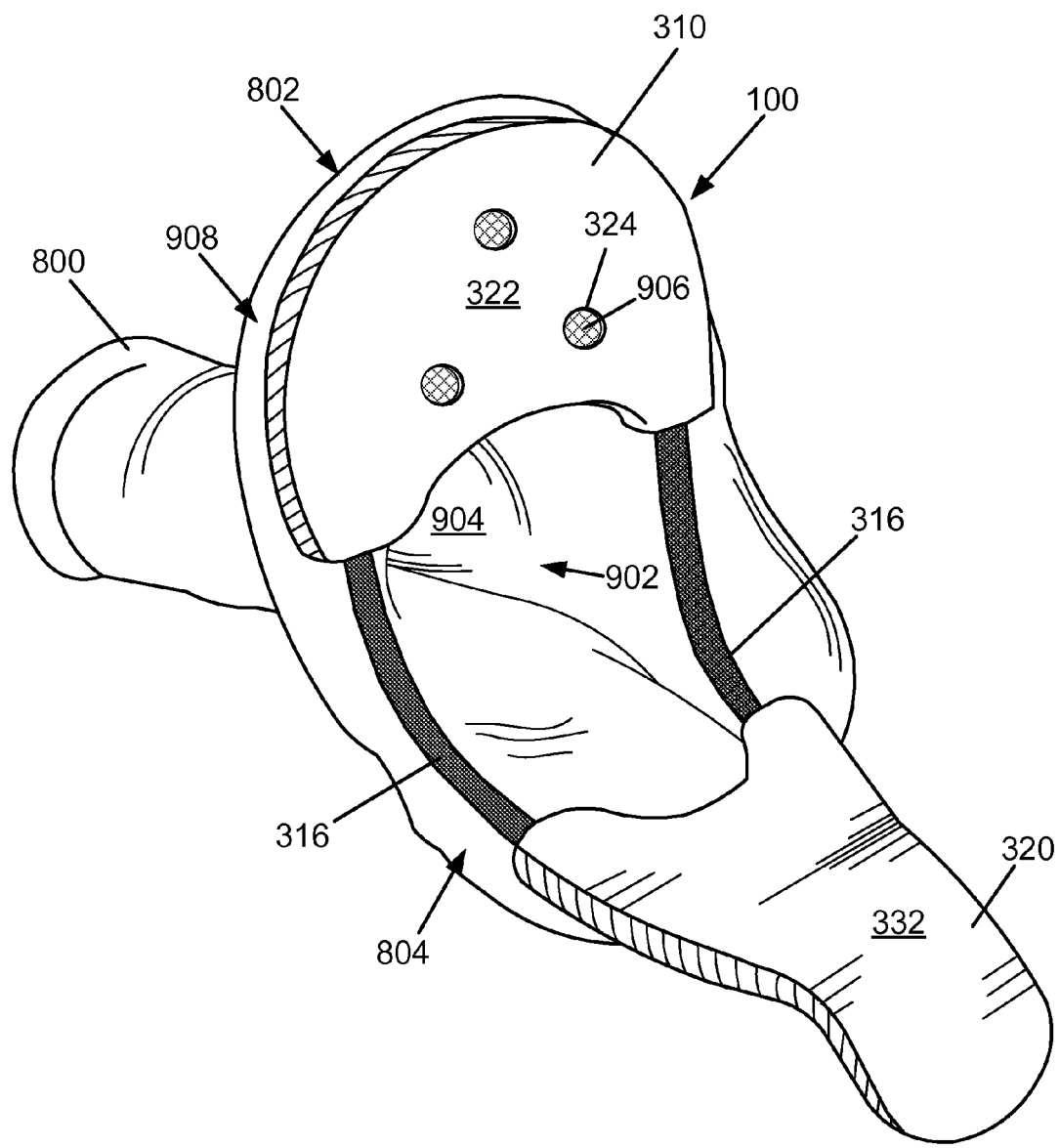
FIG. 9 illustrates a rear perspective view of a pelvic harness coupled to an extender.

FIG. 9 illustrates a rear perspective view of the pelvic harness 100 coupled to the extender 800. As described above, the extender 800 includes a securement flap 802 that is coupled to the second surface 422 (see FIG. 4) of the pelvic harness' tab 310. Specifically, the second surface 422 may be secured to a first surface 908 of the flap 802. According to one embodiment, the first surface 908 of the flap 802 may be glued to the second surface 422 of the tab 310 using an adhesive, such as acrylic, rubber, and/or plastic cement. Cyanoacrylate (e.g., Super Glue®) may also be used as an adhesive. According to another embodiment, the second surface 422 may be secured to the first surface 908 using fasteners (e.g., nuts and bolts). Adhesives and/or fasteners may be selected and used so that the dildo 800 is removeably coupled to the pelvic harness 100.

The tab 310 may have one or more holes 324 that assist with adhering the dildo 800 to the tab's second surface 422. For example, the holes 324 allow adhesive material 906 applied between the second surface 422 and the securement flap's first surface 908 to flow through and bond to the inner cavity walls of the holes 324. In some embodiments, the securement flap's first surface 908 may include corresponding raised bumps (not shown) that match up with and are inserted into the holes 324 of the tab 310. This may increase the surface area of material having adhesive on it to better secure the dildo 800 to the pelvic harness 100. In the embodiment shown in FIG. 9, the pelvic harness 100 features three (3) holes 324. However, in other embodiments the pelvic harness 100 may comprise more or less holes 124, including zero (0).

In the example illustrated, the penis-shaped extender 800 has an opening 902 at its distal end that allows a male user to insert his biological penis into the cavity 904 of the partially hollow extender 800. When worn, the extender 800 serves as an extension of the user's penis. In this fashion, a male user may pass his penis and testicles through the rails 316, insert his penis into the extender's cavity 904, secure the first surface 322 of the tab 310 against his superior pubic skin region, secure the first surface 332 of the saddle 320 to his perineal-anal region, and then proceed to engage in, for example, sexual intercourse with one or more partners. In other embodiments, the dildo 800 may be a solid dildo (i.e., lacking an opening 902 and cavity 904) that may be worn, for example, by a female user. In that case, the female user does not necessarily pass any body parts through the rails 316, and simply secures the first surface 322 of the tab 310 against her superior pubic skin region, secures the first surface 332 of the saddle 320 to her perineal-anal region, and then proceeds to engage in, for example, sexual intercourse with one or more partners. A medical adhesive, such as BT-460 manufactured by Factor II, Incorporated, may be used to secure the tab's first surface 322 to the user's superior pubic skin region and the saddle's first surface 332 to at least a portion of the user's perineal-anal region.

Figure 10:
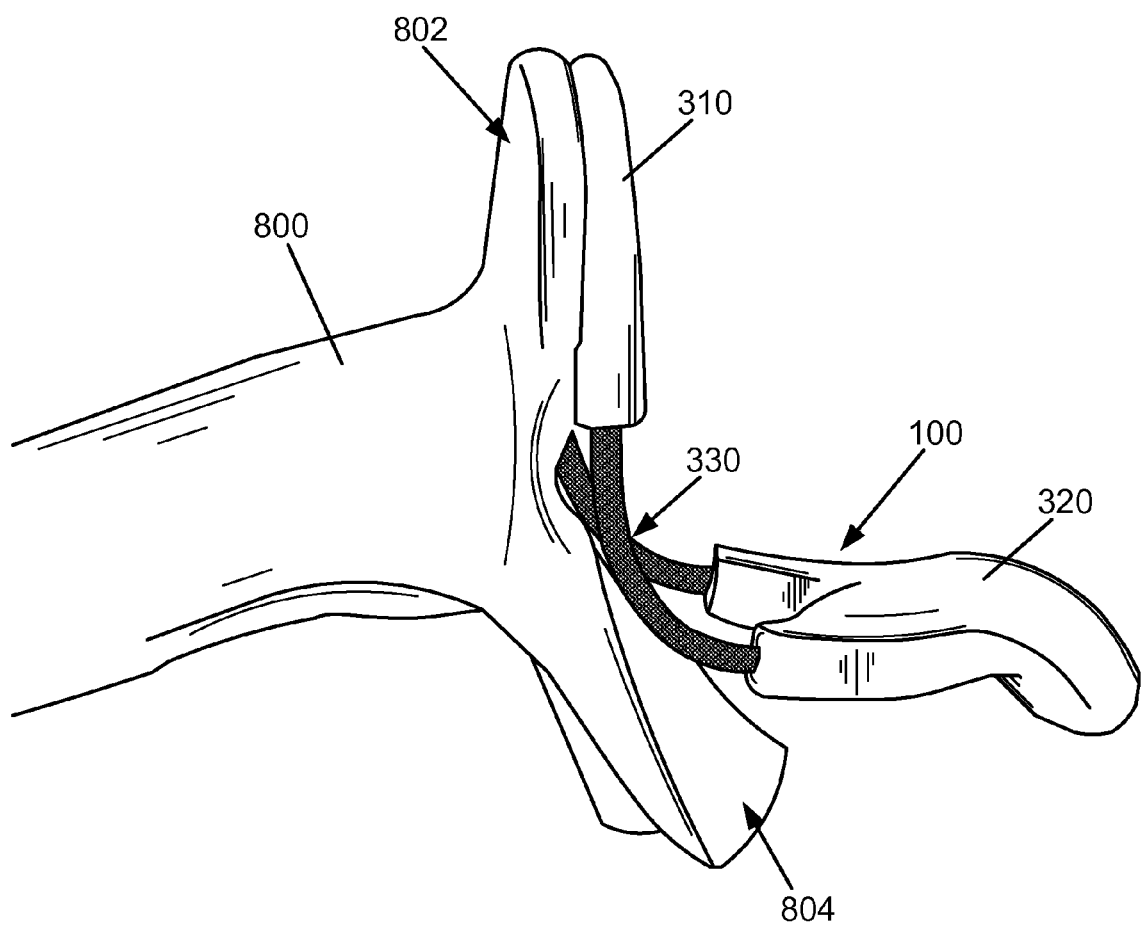
FIGS. 10-12 illustrate various views of a pelvic harness coupled to an extender.
Figure 11:
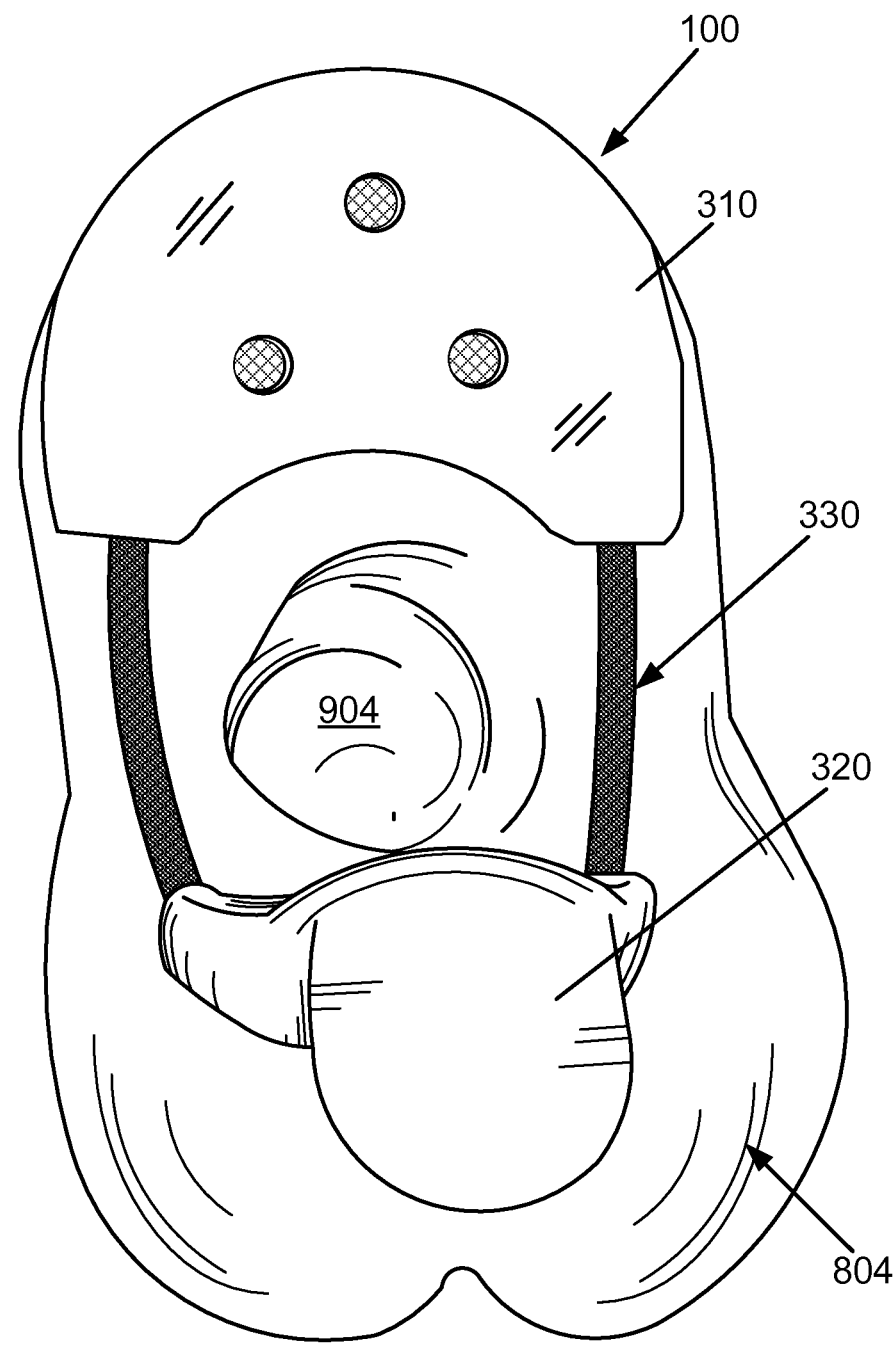
Figure 12:
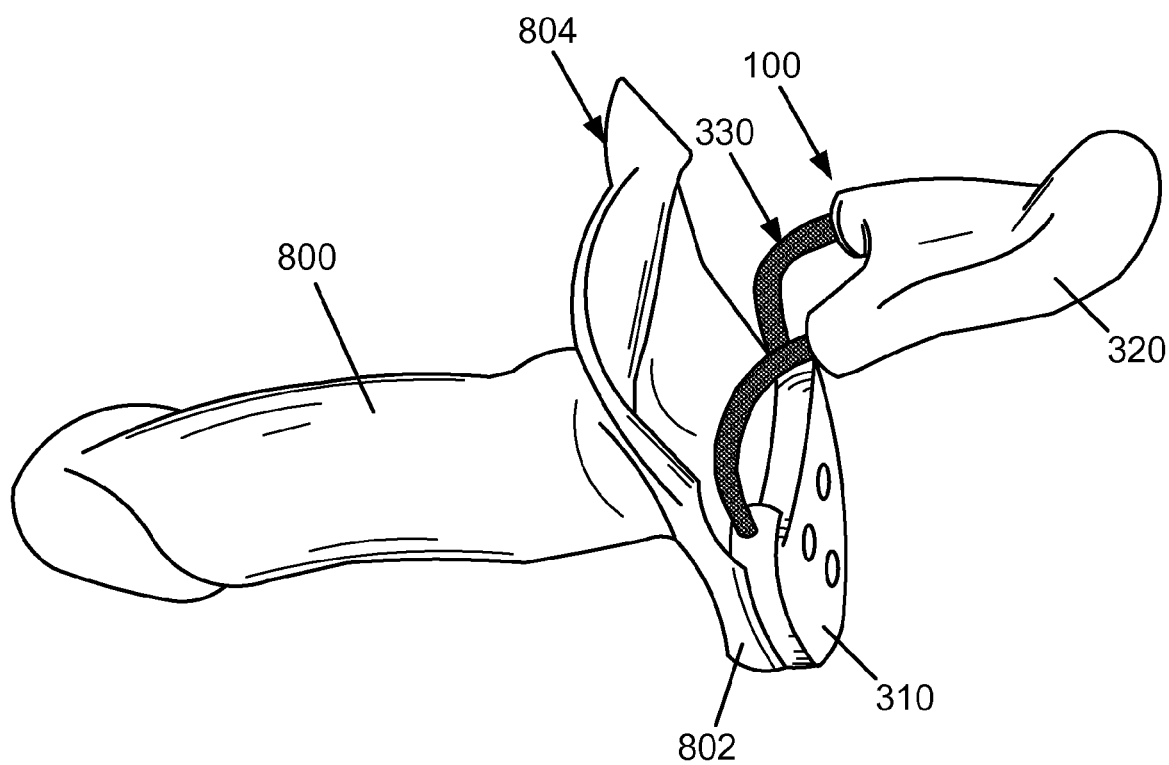

FIGS. 10-12 illustrate various views of the pelvic harness 100 coupled to the extender 800. FIG. 10 illustrates a side perspective view of the pelvic harness 100 coupled to the extender 800. FIG. 11 illustrates a rear view of the pelvic harness 100 coupled to the extender 800. FIG. 12 illustrates a bottom perspective view of the pelvic harness 100 coupled to the extender 800.

Figure 13:
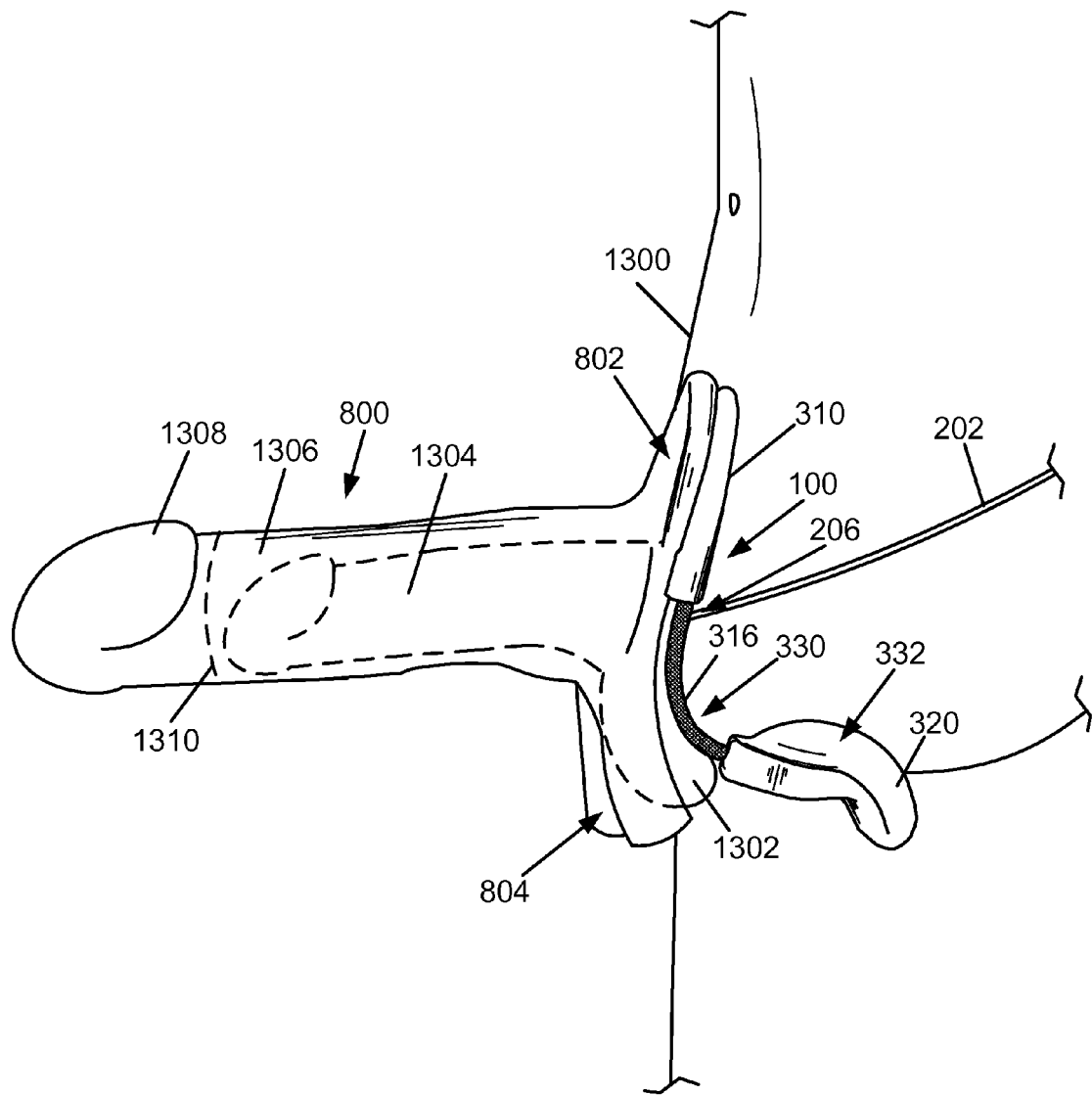
FIG. 13 illustrates a schematic side view of a male user wearing the pelvic harness and an extender.

FIG. 13 illustrates a schematic side view of a male user 1300 wearing the pelvic harness 100 and extender 800 according to one embodiment. In the illustrated example, the user's biological scrotum 1302 and penis 1304 pass through the rails 316 of the pelvic harness 100. The tab 310 is pressed against the user's superior pubic skin region (e.g., pubic symphysis region), and the saddle 320 is pressed against at least a portion of the user's perineal-anal region. The user's biological penis 1304 is inserted into and rests within the hollow portion/cavity 1306 of the extender 800. In the illustrated example, the tip (e.g., proximal end) 1308 of the extender 800 is solid and partitioned off from the hollow cavity 1306 by the extender inner cavity wall 1310. In at least one embodiment, a medical adhesive (such as but not limited to BT-460 manufactured by Factor II, Incorporated) may be used to bond the first surface 322 (See FIG. 3) of the tab 310 to the user's superior pubic skin region. In another embodiment, a medical adhesive may be used to bond the first surface 332 of the saddle 320 to the user's perineal-anal region.

The rails 316 of the pelvic harness 100 may be longer or shorter depending on what portion of the perineal-anal region the saddle 320 is to secure to. For example, the rails 316 may be relatively shorter if the saddle 320 is to press against the perineum. The rails 316 may be relatively longer if the saddle 320 is to press against the anus, the intergluteal cleft, and/or the buttocks. Thus, the rails 316 of the frame 330 may be fabricated to any length so that the saddle 320 rests anywhere along the user's perineal-anal region no matter the gender or size of the user. Moreover, the tab 310, the saddle 320, and the frame 330 of the pelvic harness 100 may be produced in a large variety of sizes to accommodate users of different proportions. In the illustrated example, an optional strap 202 may be wrapped around the user's waist and/or buttocks such that each end 204, 206 (see for example FIG. 2) of the strap 202 is coupled to each of the rails 316 of the rail portion 315 (see FIG. 3). The optional strap 202 may assist in stabilizing the pelvic harness 100, but is not necessary.

Rail Accessories

Figure 14:
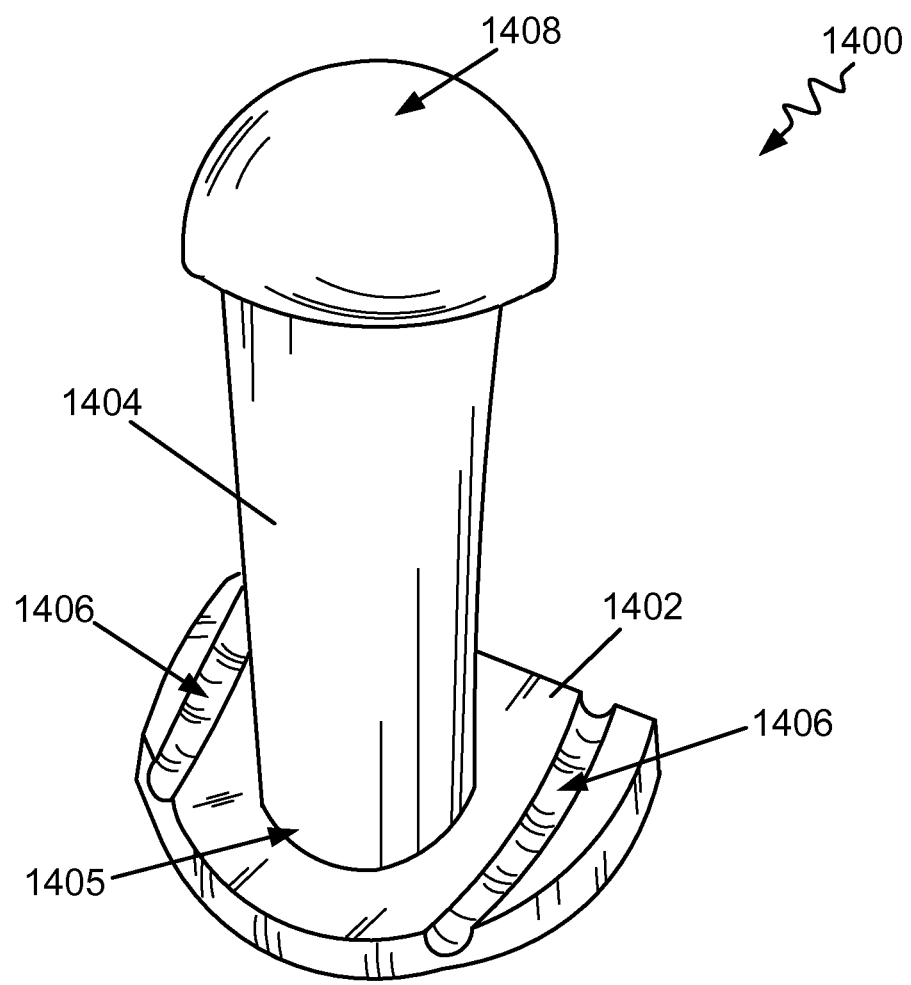
FIG. 14 illustrates a top perspective view of a rail accessory.

FIG. 14 illustrates a top perspective view of a rail accessory 1400 according to one embodiment. The rail accessory 1400 comprises a rail accessory base 1402 and a secondary accessory 1404, such as another (e.g., secondary) dildo. The rail accessory base 1402 may be composed of silicone, rubber, plastic, wood, glass, or metal. The base 1402 features one or more rail channels 1406 that are adapted to removeably couple to the rails 316 of the pelvic harness 100 in order to secure the rail accessory 1400 to the pelvic harness 100. The rail channels 1406 may be elongate grooves carved into the rail accessory base 1402 that have a substantially semi-circular cross section.

The secondary dildo 1404 may be composed of a similar material as the primary dildo 800 shown in FIG. 8. Referring to FIG. 14, the secondary dildo 1404 may be made of soft silicone rubber, plastic, silicone, wood, rubber, glass, or metal. The secondary dildo 1404 has a distal end 1405 that couples to the rail accessory base 1402, for example, with an adhesive bond. The secondary dildo 1404 also has a proximal end 1408 that may or may not have a bulge (e.g., mushroom-shaped tip). In the illustrated example, the proximal end 1408 includes the bulge, which may help keep the secondary dildo 1400 lodged within an orifice (e.g., vagina, anus, etc.) of a user. According to one embodiment, the rail accessory base 1402 and the secondary accessory 1404 are one piece molded together, while in another embodiment, the secondary accessory 1404 may be removeably coupled to the rail accessory base 1402.

Figure 15:
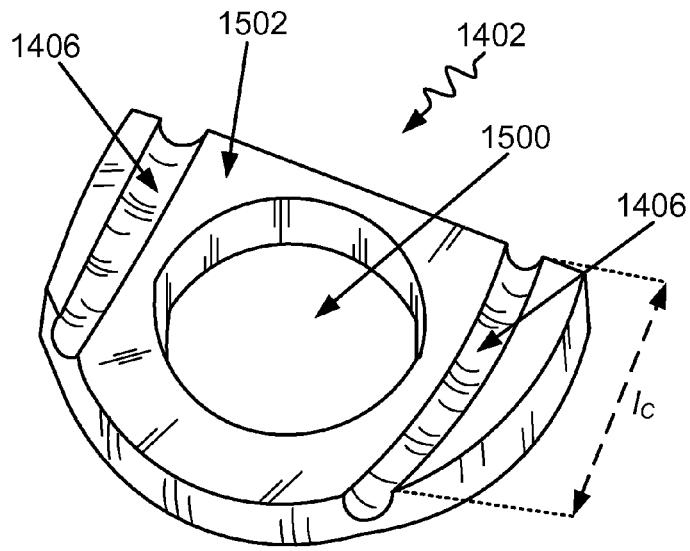
FIG. 15 illustrates a top perspective view of a rail accessory base.

FIG. 15 illustrates a top perspective view of the rail accessory base 1402 according to one embodiment. The rail accessory base 1402 includes the rail channels 1406 and may include a base opening 1500. As shown, the rail channels 1406 are located on a first surface 1502 of the rail accessory base 1402 (i.e., the opening to the rail channels 1406 is located on the first surface 1502). The rail channels 1406 have lengths $l_C$ that are substantially parallel to one another. When the rail channels 1406 are secured to the pelvic harness wires 316, the lengths $l_C$ also are oriented substantially parallel to the lengths of the wires 316.

The base opening (also may be referred to as a "rail accessory base hole") 1500 allows a plurality of different types of secondary accessories (e.g., the secondary dildo 1404) to removeably couple to the rail accessory base 1402. According to one aspect, an adhesive such as cyanoacrylate may be used to securely couple the secondary accessory 1404 to the base 1402. In other embodiments, a weaker adhesive, such as, but not limited to, a Pritt Stick® glue stick adhesive can be used to adhere the secondary accessory 1404 to the base 1402 so that the user can easily remove the accessory 1404 from the base 1402 if needed (e.g., to place another type of secondary accessory in the base opening 1500).

Figure 16A:
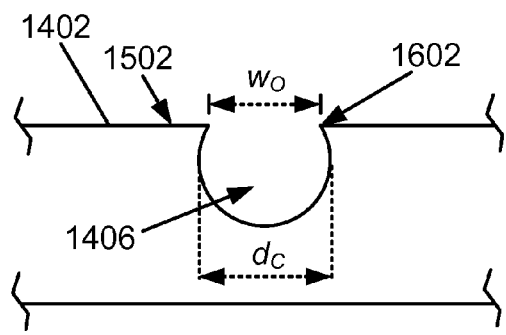
FIG. 16A illustrates a schematic, cross-sectional view of a rail channel.
Figure 16B:
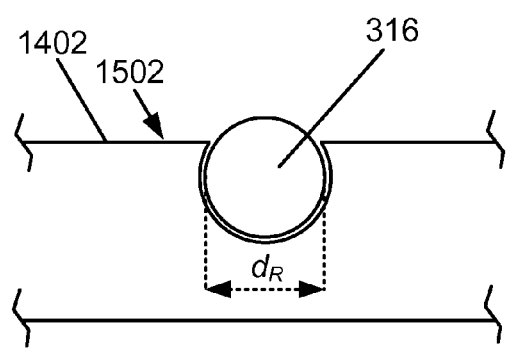
FIG. 16B illustrates a schematic, cross-sectional view of a rail channel secured to a rail.

FIG. 16A illustrates a schematic, cross-sectional view of a rail channel 1406, and FIG. 16B illustrates a schematic, cross-sectional view of the rail channel 1406 secured to a rail 316. In the illustrated examples, the rail channel 1406 has a substantially semi-circular cross section that matches the semi-circular cross section of the rail 316 so that the two can snugly, yet removeably, couple together. According to one example, the diameter $d_C$ of the rail channel 1406 may be larger than the width $w_O$ of the rail channel opening 1602. In other examples, the diameter $d_C$ of the rail channel 1406 may be the same size or smaller than the width $w_O$ of the rail channel opening 1602. If the rail channel opening's 1602 width $w_O$ is smaller than the rail channel's diameter $d_C$, then the accessory base 1402 may be made of a slightly flexible material, such as rubber. This allows the a rail 316 having a diameter $d_R$ that is larger than the rail channel width $w_O$ (but smaller than the rail channel diameter $d_C$) to squeeze into the rail channel 1406 and "snap" into place as shown in FIG. 16B. According to other embodiments, an adhesive may be applied to the rail channel 1406 to help adhere the accessory base 1402 to the rails 316.

Figure 17:
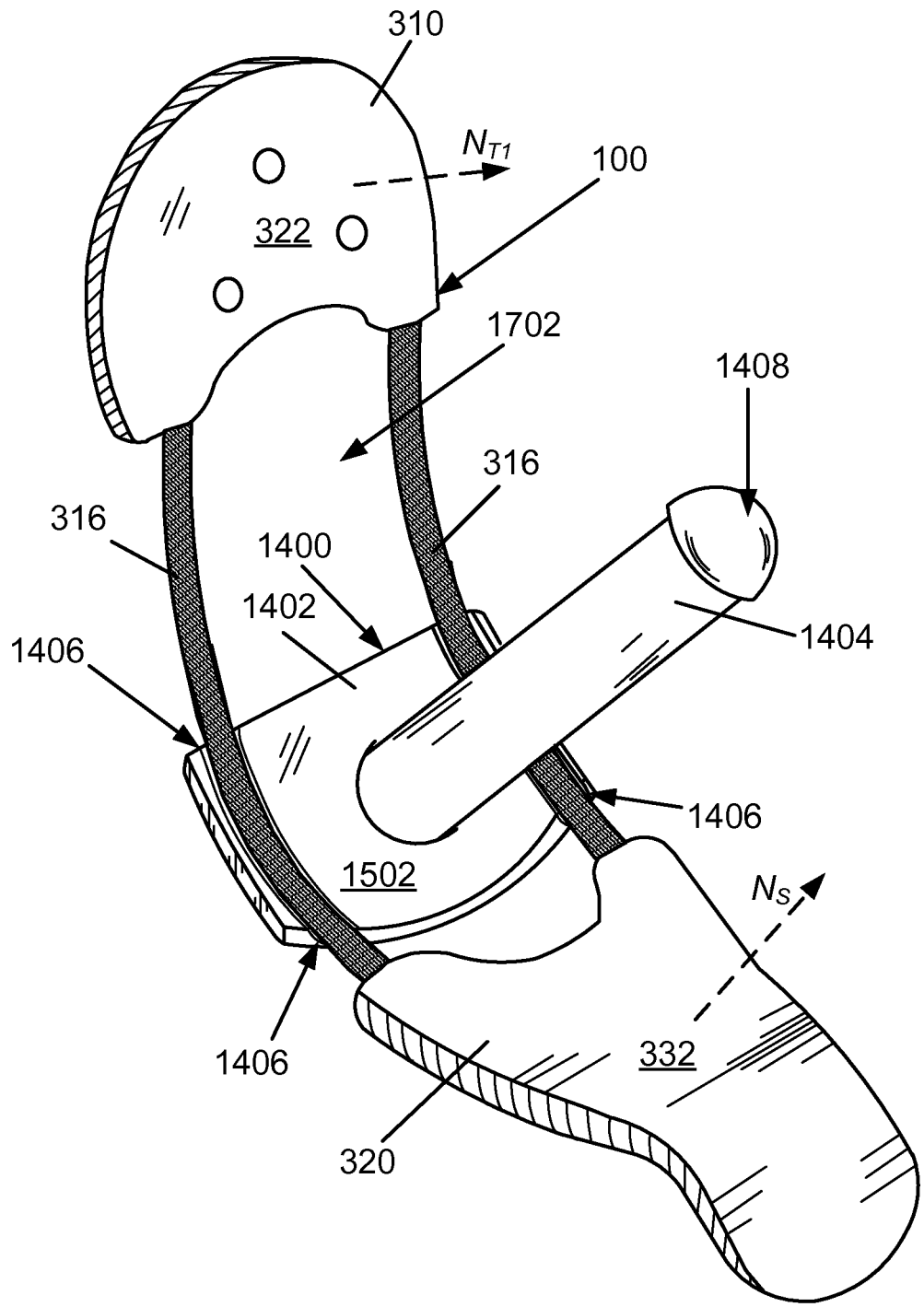
FIG. 17 illustrates a top perspective view of a rail accessory removeably coupled to a pelvic harness.

FIG. 17 illustrates a top perspective view of the rail accessory 1400 removeably coupled to the pelvic harness 100 according to one embodiment. The rail accessory 1400 includes the rail accessory base 1402 and the secondary dildo 1404. In this example, the rail accessory 1400 is removeably coupled to the pelvic harness 100 by passing the secondary dildo 1404 through the rails 316 of the pelvic harness 100, and then securing the pelvic harness rails 316 to the rail channels 1406 of the rail accessory base 1402 as shown. Once secured, the rail accessory 1400 forms a pelvic harness opening 1700 defined by the space between the rails 316, the tab 310, and the rail accessory base 1402.

The proximal end 1408 of the secondary dildo 1404 is oriented to point toward a user wearing the pelvic harness, so that the secondary dildo 1404 may be inserted into the vagina or anus of the user. That is, the proximal end 1408 of the secondary dildo 1404 may be oriented such that it generally points in a direction parallel to the normal vector $N_{T1}$ of the tab's first surface 322, a direction parallel to the normal vector $N_S$ of the saddle's first surface 332, or a direction parallel to a vector oriented in between $N_{T1}$ and $N_S$.

A user may wear the pelvic harness 100 featuring the rail accessory 1400 by: removeably coupling the rail accessory 1400 to the harness rails 316; securing the tab's first surface 322 to their superior pubic skin region; securing the saddle's first surface 332 to their perineal-anal region; and inserting the secondary dildo 1404 into their vagina or anus. If the person wearing the pelvic harness 100 is male, then he may also pass his scrotum and/or penis through the opening 1700 and insert the secondary dildo 1404 into his anus. If an extender 800 is coupled to the second surface 422 of the tab 310 (see FIGS. 4, 8, 10), then the male user may also insert his penis into the extender's cavity 904 (see FIG. 9). Referring to FIG. 17, if the user however is female, then she may not necessarily pass any organs through the opening 1700, and may simply insert the secondary dildo 1404 into either her anus or her vagina.

In one embodiment, the secondary accessory 1404 may comprise two separate elongate dildos where one is designed to be inserted into the vagina, and the other is designed to be fit into the anus of the female user at the same time. By inserting the secondary dildo 1404 into the user's vagina or anus, the dildo 1404 may provide sexual gratification to the user wearing the pelvic harness 100, while at the same time helping secure the pelvic harness 100 to the user. The user wearing the pelvic harness 100 and rail accessory 1400 may also engage in sexual intercourse with one or more partners if, for example, the pelvic harness 100 has a dildo 800 coupled to its tab's second surface 422 (see FIGS. 4, 8).

Figure 18:
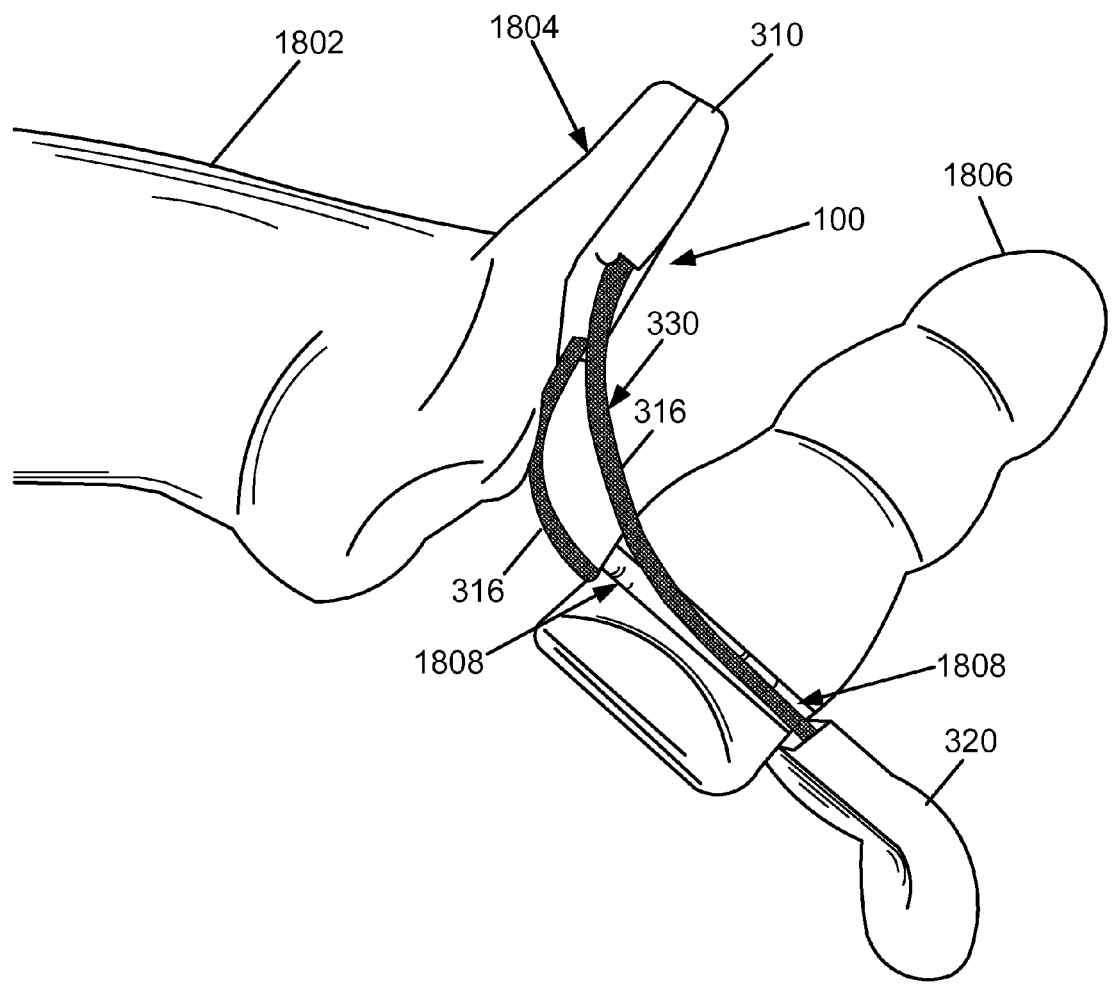
FIG. 18 illustrates a pelvic harness coupled to a primary dildo and a rail accessory.

FIG. 18 illustrates the pelvic harness 100 coupled to a primary dildo 1802 and a rail accessory 1806 according to another embodiment. In the illustrated example, the dildo 1802 may be a solid dildo that may be used for sexual activity but is not hollow like an extender. The dildo 1802 features a securement flap 1804 that secures to the back surface 422 of the tab 310 in the same way the flap 804 of the extender 800 secures to the pelvic harness 100 described above. The rail accessory 1806 may be a secondary dildo that can be inserted into the user's anus or vagina as described above with respect to FIG. 17. However, in the illustrated example, the rail accessory 1806 does not have a rail accessory base that couples to the rails 316 of the pelvic harness 100. Instead, the rail accessory 1806 directly couples to the pelvic harness rails 316. In one example, the rail accessory 1806 may have one or more rail channels 1808 that are grooves carved into the rail accessory 1806 itself to mate with the corresponding rails 316 of the pelvic harness 100. This may help secure the rail accessory 1806 to the rails 316.

Figure 19:
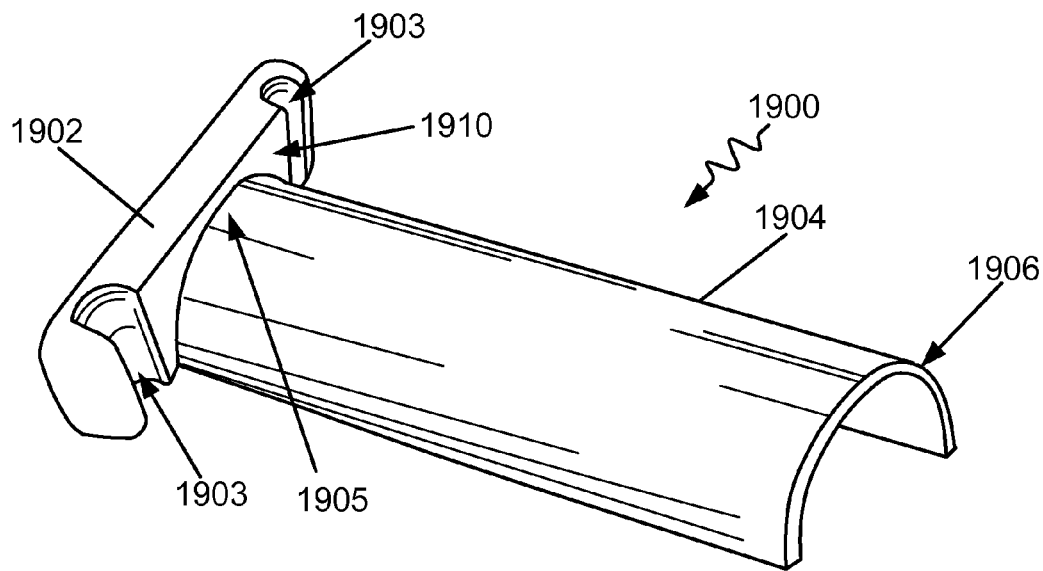
FIGS. 19 and 20 illustrate top and bottom perspective views, respectively, of a rail accessory.
Figure 20:
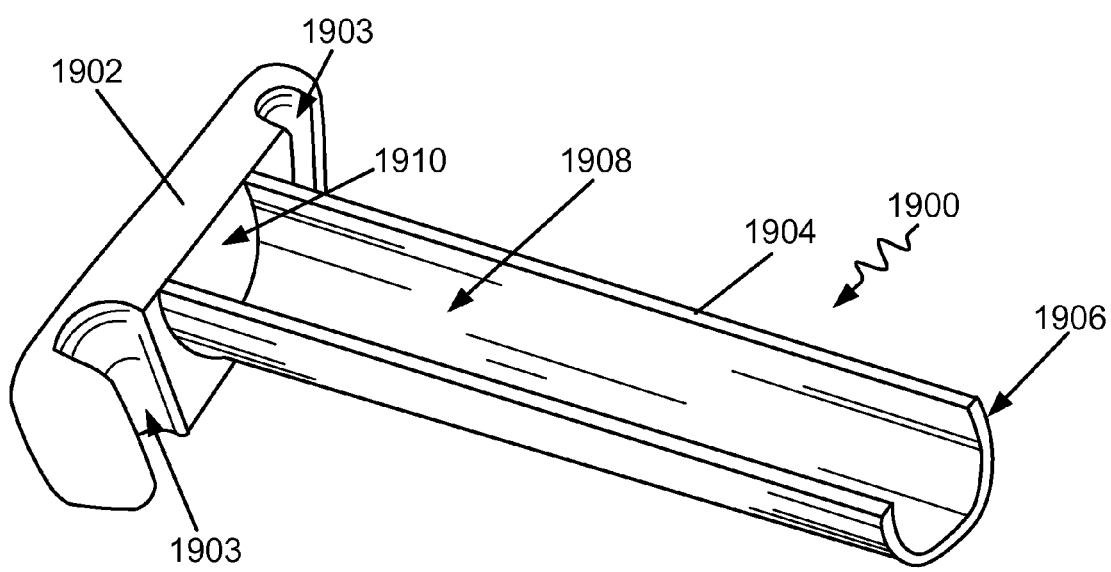

FIGS. 19 and 20 illustrate top and bottom perspective views, respectively, of a rail accessory 1900 according to another embodiment. The rail accessory 1900 comprises a rail accessory base 1902 and a secondary accessory 1904, such as an extender erection accessory. The rail accessory base 1902 may be composed of silicone, rubber, plastic, wood, glass, or metal. The base 1902 features one or more rail channels 1903 that are adapted to removeably couple to the rails 316 of the pelvic harness 100 in order to secure the rail accessory 1900 to the pelvic harness 100. The rail channels 1903 may be elongate grooves carved into the rail accessory base 1902 that have a substantially semi-circular cross section. According to one embodiment, the rail accessory base 1902 and the secondary accessory 1904 are one piece molded together, while in another embodiment, the secondary accessory 1904 may be removeably coupled to the rail accessory base 1902.

The extender erection accessory 1904 has an elongate, hollow shaft that may be composed of a rigid material such as plastic, wood, or metal, and features a curved cross-section (e.g., semi-circle or quarter-circle cross-section). As explained in greater detail below, the accessory's 1904 elongate, curved shaft forms an extender accessory cavity 1908 that is large enough to accommodate a user's penis. Referring to FIGS. 9, 19, and 20, the extender erection accessory 1904 includes a distal end 1905 that couples to the rail accessory base 1902 (e.g., at the first surface 1910), and a proximal end 1906 that may be inserted into the hollow cavity 904 of an extender 800. The extender erection accessory 1904 provides a means for keeping the extender 800 erect (e.g., pointing at an a generally upward angle and substantially straight) even if the biological penis of the user wearing the pelvic harness 100 and extender 800 is limp. Once the extender erection accessory 1904 is inserted into the extender cavity 904, the extender accessory cavity 1908 allows room for the user's biological penis to be inserted into the extender cavity 904 as well.

The rail channels 1903 and the rail accessory base 1902 itself may be substantially similar in design and function to the rail channels 1406 and the rail accessory base 1402 described above with respect to FIGS. 15, 16A, and 16B. For example, the rail channels 1903 located on the base's first surface 1910 may also feature an opening that is slightly smaller than the rail channel's diameter so that the rails 316 of the pelvic harness 100 "snap" into place when securing the rail accessory base 1902 to the harness' frame 330. All embodiments of the rail accessory base 1402 described above equally apply to the rail accessory base 1902 of FIGS. 19-21.

Figure 21:
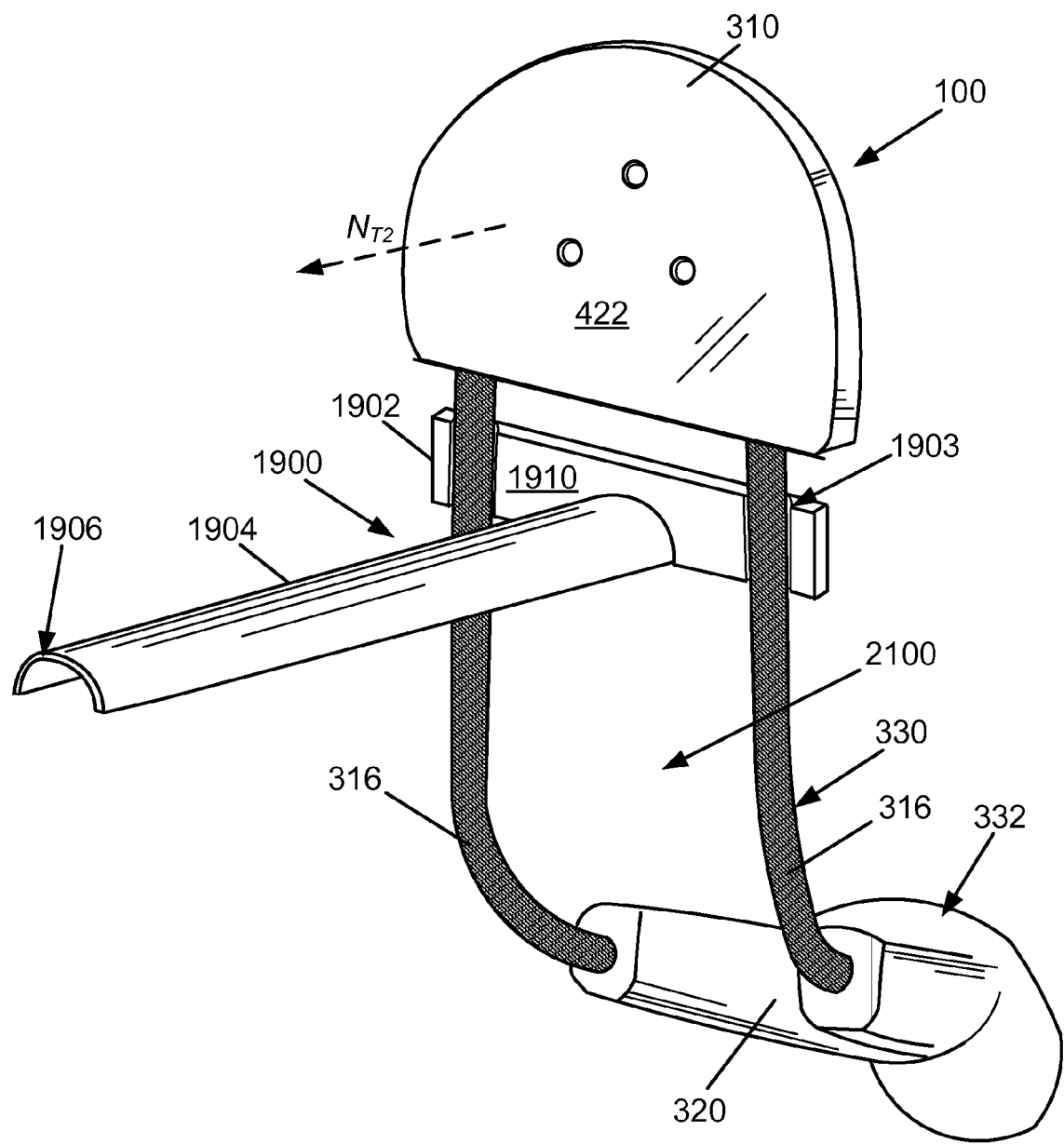
FIG. 21 illustrates a perspective view of a rail accessory removeably coupled to a pelvic harness.

FIG. 21 illustrates a perspective view of the rail accessory 1900 removeably coupled to the pelvic harness 100 according to one embodiment. The rail accessory 1900 includes the rail accessory base 1902 and the extender erection accessory 1904. In this example, the rail accessory 1900 is removeably coupled to the pelvic harness 100 by passing the extender erection accessory 1904 through the rails 316 of the pelvic harness 100, and then securing the pelvic harness rails 316 to the rail channels 1903 of the rail accessory base 1902 as shown. Once secured, the rail accessory 1900 forms a pelvic harness opening 2100 defined by the space between the rails 316, the saddle 320, and the rail accessory base 1402.

The proximal end 1906 of the extender erection accessory 1904 is oriented to point away from a user wearing the pelvic harness 100, so that the extender erection accessory 1904 may be inserted into the cavity 904 of an extender 800 (see for example FIG. 9) attached to the second surface 422 of the pelvic harness tab 310. (For the sake of clarity, the extender 800 is not shown in FIG. 21.) For example, the proximal end 1906 of the extender erection accessory 1904 may be oriented such that it generally points in a direction parallel to the normal vector N of the tab's second surface 422.

A user may wear the pelvic harness 100 featuring the rail accessory 1900 by: removeably coupling the rail accessory 1900 to the harness rails 316; inserting the proximal end 1906 and shaft of the extender erection accessory 1904 into the extender cavity 904; securing the tab's first surface 322 (not shown in FIG. 21) to their superior pubic skin region; and securing the saddle's first surface 332 to their perineal-anal region. If the person wearing the pelvic harness 100 is male, then he may also pass his scrotum and/or penis through the opening 2100 and his penis into the extender cavity 904. The extender accessory cavity 1908 (see FIG. 20) provides additional room within the extender cavity 904 to accommodate the user's penis. If, however, the user is female then she may not necessarily pass any organs through the opening 2100, and may simply use the pelvic harness 100 coupled to the rail accessory 1900 without inserting anything else into the extender cavity 904. In this fashion, a user may engage in sexual activity using the extender 800 regardless of whether the user's penis is flaccid or erect, or whether the user even has a penis.

Other Embodiments

Figure 22:
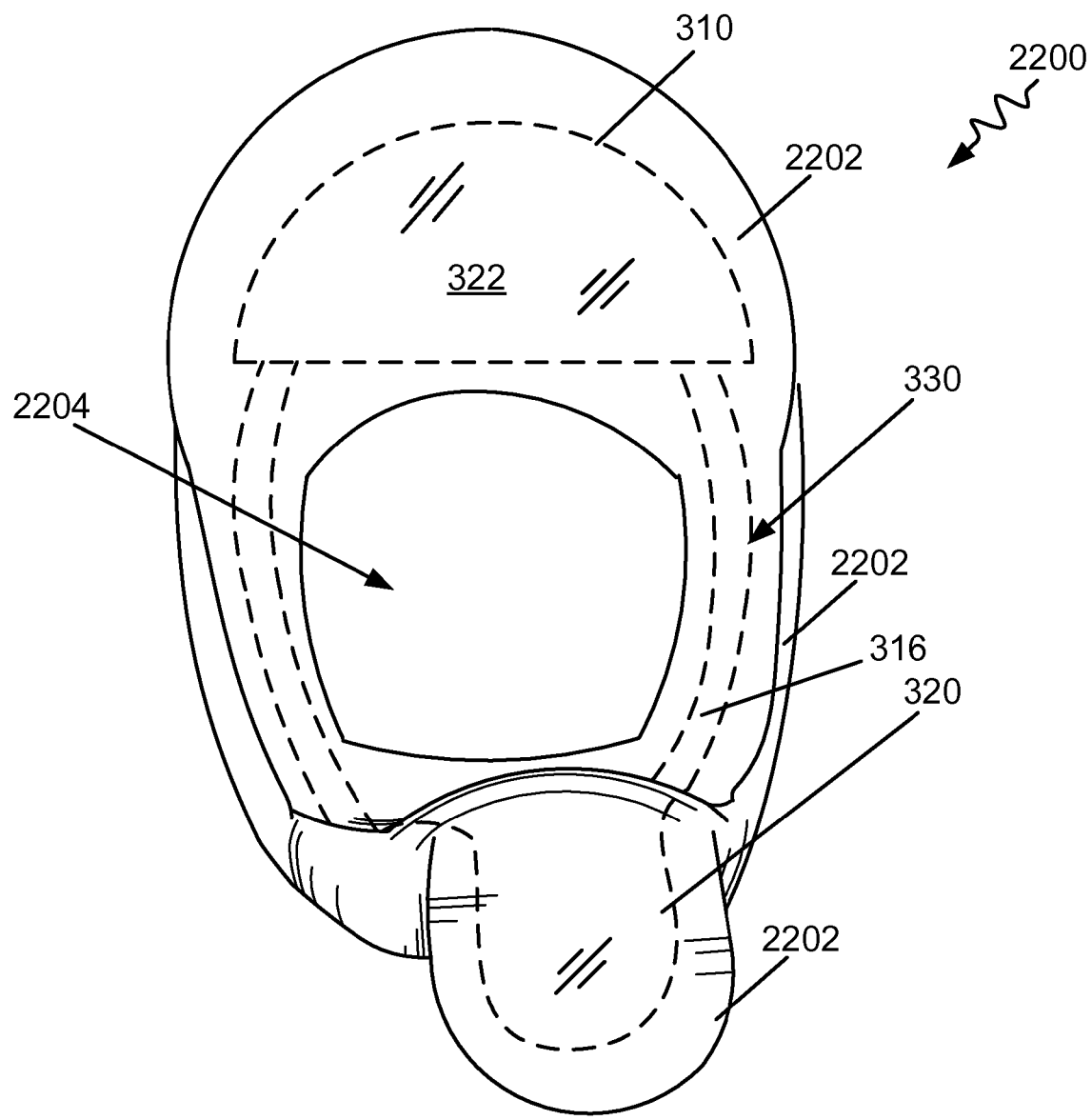
FIGS. 22 and 23 illustrate a front view and a side view, respectively, of a pelvic harness encased in silicone.
Figure 23:
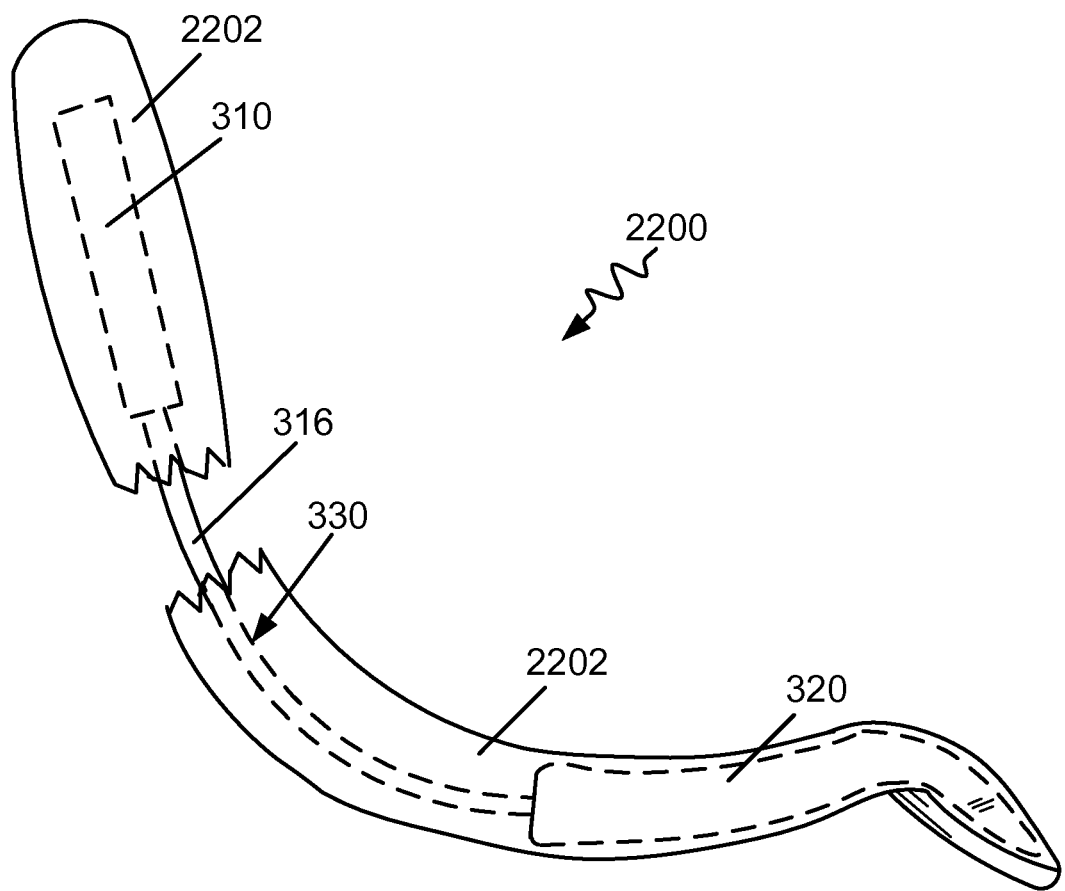

FIGS. 22 and 23 illustrate a front view and a side view, respectively, of a pelvic harness 2200 encased in silicone according to one embodiment. The harness 2200 comprises a tab 310, a saddle 320, and a frame 330 covered in (i.e., encased in) silicone 2202 for a softer, more comfortable fit. A male user may pass his scrotum and/or penis through a pelvic harness opening 2204 defined by the silicone 2202 surrounding the rails 316, the tab 310, and the saddle 320. Referring to FIG. 23, a portion of the silicone 2202 covering the frame 330 has been omitted to reveal one of two rails 316 underneath. The frame 330 is bendable/flexible to allow the tab 310 to bend toward, bend away from, and/or twist relative to the saddle 320 as previously described with respect to the pelvic harness 100 shown in FIG. 6.

According to one aspect, the silicone 2202 encases the entire pelvic harness 2200. According to another embodiment, the silicone 2202 only covers a portion of the pelvic harness 220, such as, but not limited to, covering the saddle 320, the rails 316, the tab 310, and/or the first surface 322 of the tab 310. In that case other portions of the pelvic harness 2200 are not covered in the silicone, such as, but not limited to, the second surface 422 (not shown in FIG. 22 or FIG. 23) on the opposite side of the tab 310 (see for example the second surface 422 of the harness 100 shown in FIG. 4). According to one embodiment, a portion of the rails 316 may also not be covered in silicone to allow a rail accessory 1400, 1900 to be coupled to the rails 316.

Figure 24:
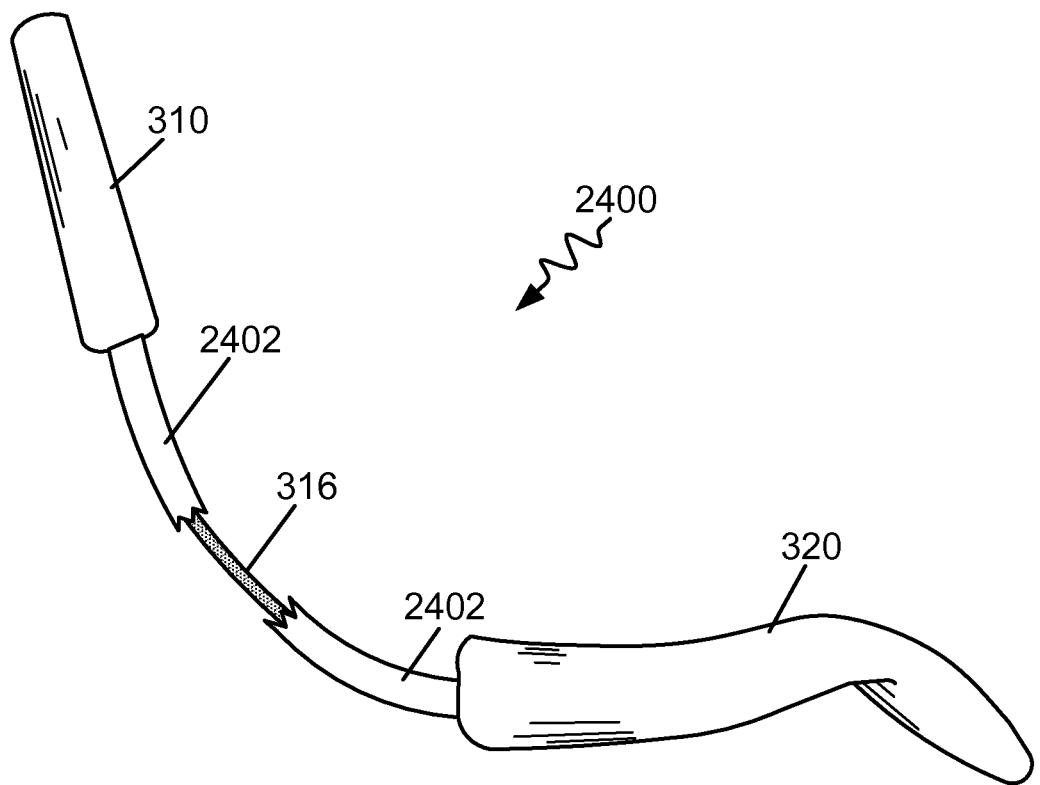
FIG. 24 illustrates a side view of a pelvic harness.

FIG. 24 illustrates a side view of a pelvic harness 2400 according to another embodiment. The pelvic harness 2400 is identical to the pelvic harness 100 illustrated in FIG. 3, except that the rails 316 are covered with a plastic sheath 2402. The plastic sheath 2402 may be adhered to the rails 316 using a heat source. The sheath 2042 protects the user from making skin contact with the metal since some users may be allergic. The sheath 2402 also may be softer to the touch and feel warmer than the metal rail 316. Note that a portion of the sheath 2402 has been removed to show the rail 316 underneath.

Figure 25:
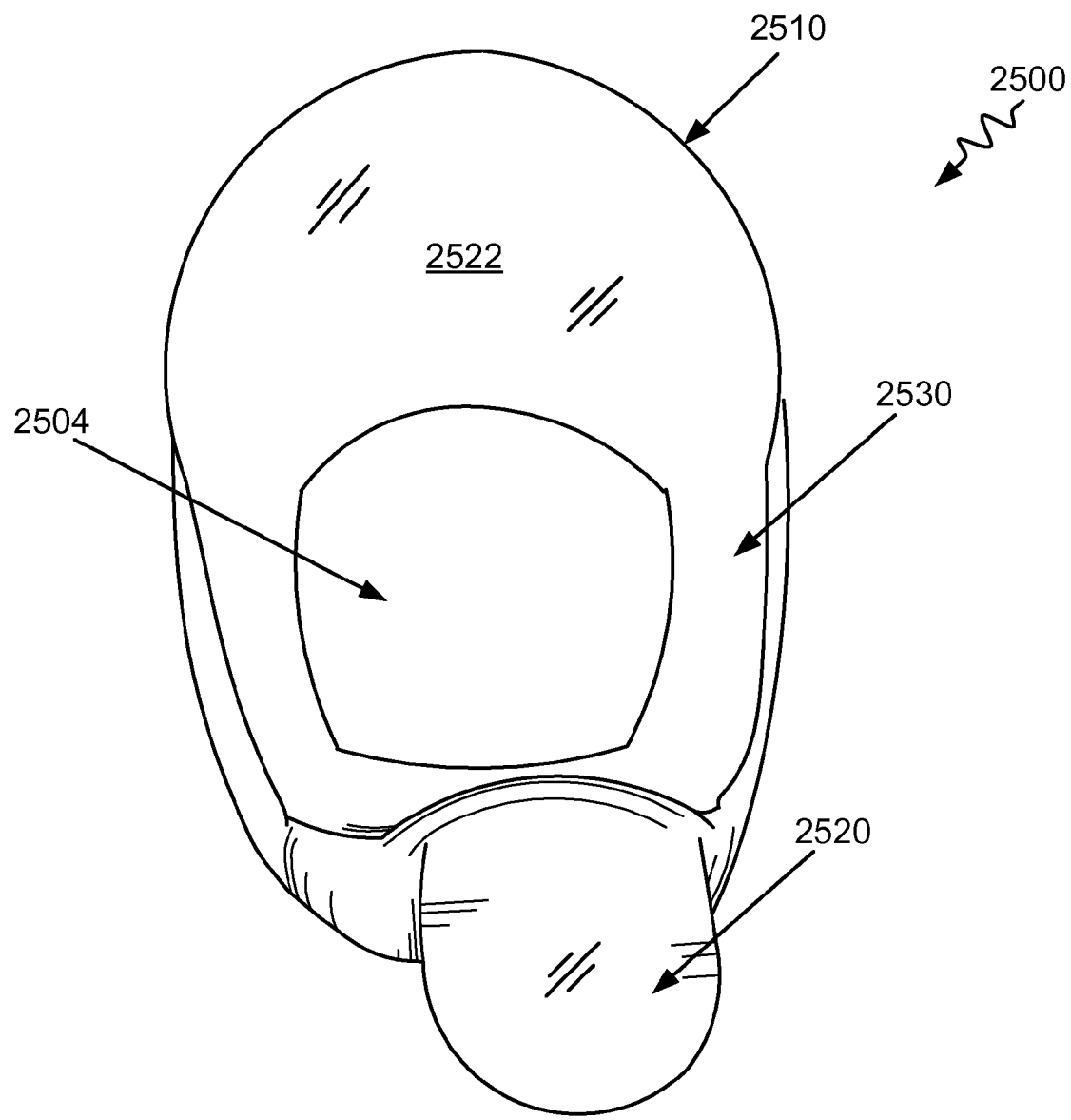
FIG. 25 illustrates a pelvic harness.

FIG. 25 illustrates a pelvic harness 2500 according to one embodiment. The harness 2500 is a single molded piece that includes a tab 2510, a saddle 2520, and a middle portion 2530. The tab 2510 features a first surface 2522 that is adapted to press against a user's superior pubic skin region. The saddle 2520 is adapted to press against at least a portion of a user's perineal-anal region. The middle portion 2530 may comprise two connecting members 2516 that define an opening 2534 and are spaced apart wide enough to allow a user to pass his scrotum and/or penis through the opening 2534.

A male user may thus wear the pelvic harness 2500 by first passing his scrotum and/or penis through the opening 2534 so that the tab's first surface 2522 comes into contact at the user's superior pubic skin region, and the saddle 2520 comes into contact with at least a portion of the user's perineal-anal region. In at least one embodiment, the harness 2500 is made of a material, such as a molded plastic, that is flexible to some degree in response to a force that exceeds a predetermined threshold such that the tab 2510 and the saddle 2520 may be bent closer or further away from each other. Moreover, the harness' 2500 flexibility also allows the connecting members 2516 to flex/bend to allow the user to more easily and comfortably pass his scrotum and/or penis through the opening 2534.

The primary dildos 800, 1802 described above may be removeably coupled to the second surface 422 of the tab 310. Adhesives may be used to permanently or removeably couple the dildos 800, 1802 to the tab's second surface 422. However, in other embodiments, locking mechanisms may be implemented to removeably couple the dildos 800, 1802 to the tab 310. For example, fasteners such as nuts and bolts may be used to couple the dildos 800, 1802 to the tab's second surface 422. Since the dildos 800, 1802 may be removeably coupled to the tab 310, a user may decide to replace a hollow extender, such as the one shown in FIG. 8, with a solid dildo, such as the one shown in FIG. 18, or vice versa. Thus, the harnesses 100, 700, 2200, 2400, 2500 allow interchangeability of dildos and other objects to the tabs. In one embodiment, a kit may include a pelvic harness 100, 700, 2200, 2400, 2500, an extender 800, a solid dildo, 1802, and one or more rail accessories 1400, 1900.

Figure 26:
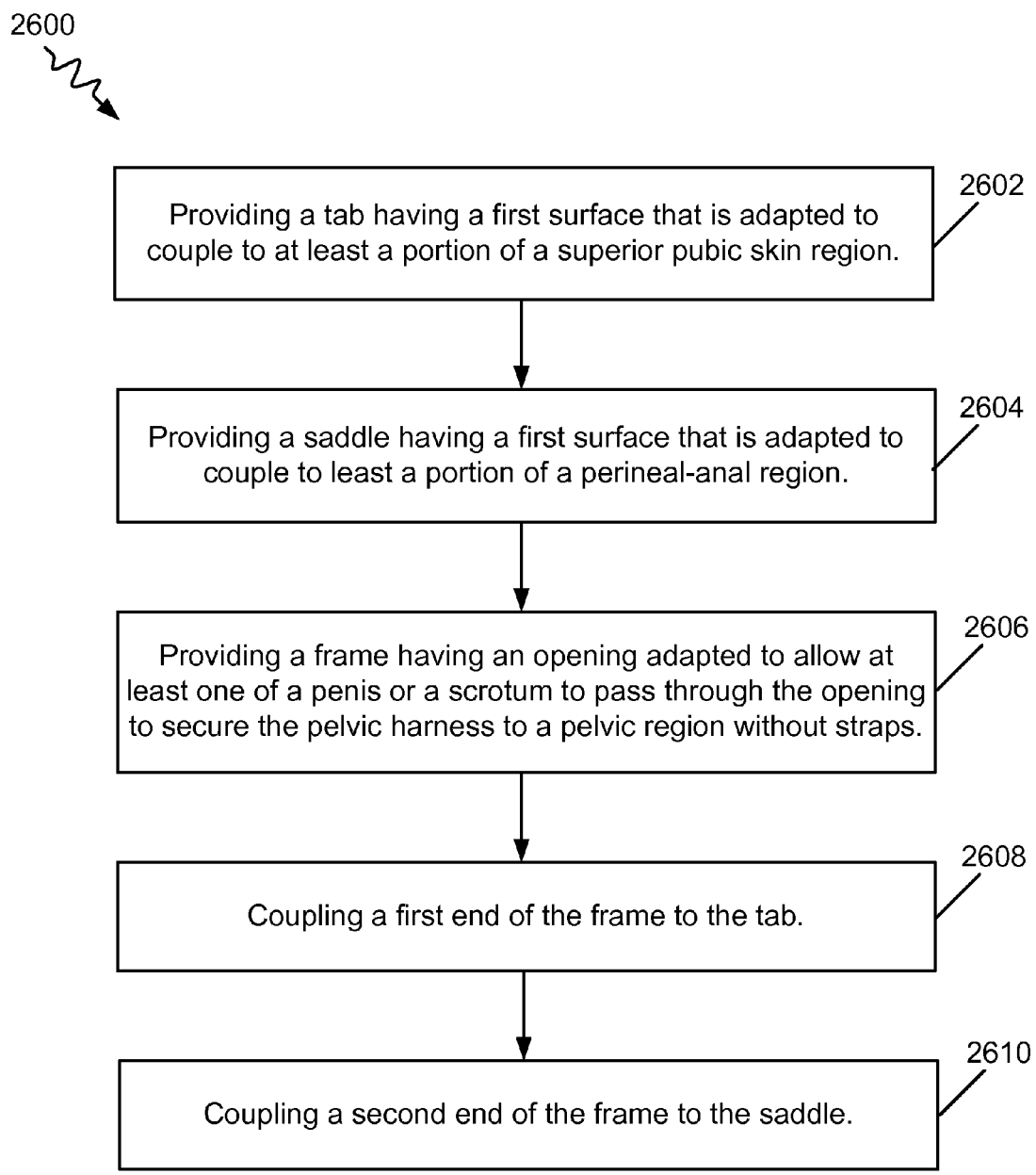
FIG. 26 illustrates a flow chart for a method of manufacturing a pelvic harness.

FIG. 26 illustrates a flow chart 2600 for a method of manufacturing a pelvic harness according to one embodiment. At step 2602, the method comprises providing a tab having a first surface that is adapted to couple to at least a portion of a superior pubic skin region. At step 2604, the method further comprises providing a saddle having a first surface that is adapted to couple to least a portion of a perineal-anal region. At step 2606, the method further comprises providing a frame having an opening adapted to allow at least one of a penis or a scrotum to pass through the opening to secure the pelvic harness to a pelvic region without straps. At step 2608, the method further comprises coupling a first end of the frame to the tab. At step 2610, the method further comprises coupling a second end of the frame to the saddle.

One or more of the components, features, and/or and functions illustrated in FIGS. 1, 2, 3, 4, 5A, 5B, 6, 7, 8, 9, 10, 11, 12, 13, 14, 15, 16A, 16B, 17, 18, 19, 20, 21, 22, 23, 24, 25, and/or 26 may be rearranged and/or combined into a single component or embodied in several components without departing from the present disclosure. Additional elements or components may also be added without departing from the present disclosure. While certain exemplary embodiments have been described and shown in the accompanying drawings, it is to be understood that such embodiments are merely illustrative of and not restrictive of the present disclosure, and that the present disclosure should not be limited to the specific constructions and arrangements shown and described, since various other modifications are possible. Therefore, it is to be understood that, within the scope of the appended claims, embodiments of the present disclosure may be practiced other than as specifically described herein.

What is claimed is:

1. A pelvic harness, comprising:
   a frame;
   a tab having a first planar surface and a second planar surface opposite the first planar surface, the first planar surface adapted to secure to at least a portion of a superior pubic skin region, the second planar surface adapted to couple to a dildo, the tab positioned at a first portion of the frame; and
   a saddle having a first convex surface with a vertex that is adapted to secure to at least a portion of a perineum, the saddle positioned at a second portion of the frame.

2. The pelvic harness of claim 1, further comprising:
   an opening positioned in between the tab and the saddle, the opening adapted to allow at least one of a penis or a scrotum to pass through the opening to secure the pelvic harness to a pelvic region.

3. The pelvic harness of claim 1, wherein a portion of the frame forms an opening positioned in between the tab and the saddle and the opening is adapted to allow at least one of a penis or a scrotum to pass through the opening to secure the pelvic harness to a pelvic region.

4. The pelvic harness of claim 3, wherein the frame is flexible and adapted to bend in response to a force exceeding a predefined threshold to allow the pelvic harness to fit one or more contours of a pelvic region.

5. The pelvic harness of claim 3, wherein the frame comprises a wire loop having a first end encased within the tab and a second end encased within the saddle, and a rail portion of the wire loop not encased by the tab or the saddle forms at least two rails that define, in part, the opening.

6. The pelvic harness of claim 3, wherein the frame comprises at least two wires each having a first end encased within the tab and a second end encased within the saddle, and a rail portion of the two wires not encased by the tab or the saddle defines, in part, the opening.

7. The pelvic harness of claim 3, wherein the frame comprises a rail portion that includes at least two rails that define, in part, the opening, and at least a first rail of the two rails is adapted to removeably couple to at least one rail accessory to secure the rail accessory to the pelvic harness.

8. The pelvic harness of claim 7, wherein at least the first rail removeably couples to at least one rail accessory, and the rail accessory includes an accessory base having at least one rail receiver that removeably couples to the first rail, and the rail accessory further includes a secondary accessory coupled to the accessory base.

9. The pelvic harness of claim 8, wherein the secondary accessory is a secondary dildo adapted to be inserted into an anus or a vagina of a user wearing the pelvic harness.

10. The pelvic harness of claim 8, wherein the secondary accessory is an extender erection accessory having an elongate shaft, the elongate shaft having a distal end that couples to the accessory base and a proximal end that is adapted to be inserted into a cavity of an extender dildo, the extender dildo coupled to a second surface of the tab, the extender erection accessory adapted to provide rigidity to the extender dildo.

11. The pelvic harness of claim 10, wherein the elongate shaft has a curved cross section that forms an extender accessory cavity that is adapted to receive a penis, the extender accessory cavity allowing the penis and the extender erection accessory to both be inserted into the cavity of the extender dildo.

12. A pelvic harness, comprising:
a frame having a first end and a second end;
a tab encasing the first end of the frame, the tab having a first surface adapted to couple to an area of skin associated with at least one of a hypogastrium, a pubic symphysis, or a pubis bone, the tab having a second surface opposite the first surface, the second surface securing a dildo;
a saddle encasing the second end of the frame, the saddle having a first convex surface having a vertex adapted to secure to at least a portion of a perineal-anal region; and
an opening in between the tab and the saddle, the opening adapted to allow at least one of a penis or a scrotum to pass through the opening to secure the pelvic harness to a pelvic region without straps.

13. The pelvic harness of claim 12, wherein the dildo is an extender having a cavity, and the opening is further adapted to allow the penis to pass through the opening and enter the cavity of the extender.

14. The pelvic harness of claim 12, wherein a portion of the frame forms the opening in between the tab and the saddle.

15. The pelvic harness of claim 14, wherein the frame is flexible to allow the tab to bend or twist relative to the saddle.

16. The pelvic harness of claim 14, wherein the frame comprises a rail portion that includes at least two rails that define, in part, the opening, and at least a first rail of the two rails is adapted to removeably couple to at least one rail accessory to secure the rail accessory to the pelvic harness.

17. A method of manufacturing a pelvic harness, the method comprising:
providing a tab having a first planar surface that is adapted to couple to at least a portion of a superior pubic skin region, the tab having a second planar surface opposite the first planar surface, the second planar surface of the tab adapted to removeably couple to a dildo;
providing a saddle having a first convex surface having a vertex that is adapted to couple to least a portion of a perineum;
providing a frame having an opening adapted to allow at least one of a penis or a scrotum to pass through the opening to secure the pelvic harness to a pelvic region without straps;
coupling a first end of the frame to the tab; and
coupling a second end of the frame to the saddle.

18. The method of claim 1, wherein the frame comprises a first rail, and the method further comprises:
providing a rail accessory that includes a rail accessory base and a secondary accessory, the rail accessory base having a rail receiver; and
removeably coupling the rail receiver to the first rail to secure the rail accessory to the pelvic harness, the secondary accessory being one of a secondary dildo or an extender erection accessory.

19. The pelvic harness of claim 1, wherein the saddle has a width and a thickness, the width of the saddle being greater than the thickness.

20. The pelvic harness of claim 2, wherein the second planar surface of the tab is coupled to an extender and the opening is adapted to allow the penis to pass through the opening and enter a cavity of the extender.

* * * * *